(12) United States Patent
Jensen et al.

(10) Patent No.: US 8,729,022 B2
(45) Date of Patent: *May 20, 2014

(54) STABILISED SOLID COMPOSITIONS OF FACTOR VII POLYPEPTIDES

(75) Inventors: Michael Bech Jensen, Allerod (DK); Birthe Lykkegaard Hansen, Vaerloese (DK); Troels Kornfelt, Virum (DK)

(73) Assignee: Novo Nordisk Healthcare AG, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/573,310

(22) Filed: Sep. 10, 2012

(65) Prior Publication Data

US 2013/0017184 A1    Jan. 17, 2013

Related U.S. Application Data

(63) Continuation of application No. 11/526,503, filed on Sep. 25, 2006, now Pat. No. 8,299,029, which is a continuation of application No. 10/609,780, filed on Jun. 30, 2003, now abandoned, which is a continuation of application No. PCT/DK03/00419, filed on Jun. 20, 2003.

(60) Provisional application No. 60/394,153, filed on Jul. 3, 2002.

(30) Foreign Application Priority Data

Jun. 21, 2002 (DK) ................................. 2002 00963

(51) Int. Cl.
*A61K 38/48* (2006.01)

(52) U.S. Cl.
USPC ...................................... 514/14.3; 424/94.3

(58) Field of Classification Search
None
See application file for complete search history.

(56) References Cited

U.S. PATENT DOCUMENTS

| | | | |
|---|---|---|---|
| 4,297,344 A | 10/1981 | Schwinn et al. | |
| 4,382,083 A | 5/1983 | Thomas | |
| 4,404,132 A | 9/1983 | Mitra | |
| 4,495,278 A | 1/1985 | Thomas | |
| 4,784,950 A | 11/1988 | Hagen et al. | |
| 4,956,386 A * | 9/1990 | McLoughlin et al. | 514/503 |
| 5,180,583 A | 1/1993 | Hedner | |
| 5,288,629 A | 2/1994 | Berkner | |
| 5,399,670 A | 3/1995 | Bhattacharya et al. | |
| 5,457,181 A | 10/1995 | Michalski et al. | |
| 5,576,291 A | 11/1996 | Curtis et al. | |
| 5,580,856 A | 12/1996 | Prestrelski et al. | |
| 5,649,959 A | 7/1997 | Hannam et al. | |
| 5,700,914 A | 12/1997 | Jorgensen et al. | |
| 5,750,358 A | 5/1998 | Morrissey | |
| 5,770,700 A | 6/1998 | Webb et al. | |
| 5,804,420 A | 9/1998 | Chan et al. | |
| 5,817,788 A | 10/1998 | Berkner et al. | |
| 5,824,780 A | 10/1998 | Curtis et al. | |
| 5,830,852 A | 11/1998 | Thatcher et al. | |
| 5,831,026 A | 11/1998 | Almstedt et al. | |
| 5,833,982 A | 11/1998 | Berkner et al. | |
| 5,874,408 A | 2/1999 | Nayar | |
| 5,925,738 A * | 7/1999 | Miekka et al. | 530/380 |
| 5,925,739 A | 7/1999 | Spira et al. | |
| 5,962,650 A | 10/1999 | Osterberg et al. | |
| 5,993,795 A | 11/1999 | Osawa et al. | |
| 6,034,222 A | 3/2000 | Fischer et al. | |
| 6,183,743 B1 | 2/2001 | Hart et al. | |
| 6,228,620 B1 | 5/2001 | Chapman et al. | |
| 6,277,828 B1 | 8/2001 | Knepp et al. | |
| 6,310,183 B1 | 10/2001 | Johannessen et al. | |
| 6,320,029 B1 | 11/2001 | Miekka et al. | |
| 6,461,610 B1 | 10/2002 | Kongsbak et al. | |
| 6,586,573 B1 | 7/2003 | Besman et al. | |
| 6,586,574 B1 | 7/2003 | Hansen | |
| 6,599,724 B1 | 7/2003 | Mikaelsson et al. | |
| 6,750,053 B1 | 6/2004 | Widrig Opalsky et al. | |
| 6,806,063 B2 | 10/2004 | Pedersen et al. | |
| 6,825,323 B2 | 11/2004 | Hess | |
| 6,833,352 B2 | 12/2004 | Johannessen et al. | |
| 6,858,587 B2 | 2/2005 | Sorensen et al. | |
| 6,903,069 B2 | 6/2005 | Pingel et al. | |

(Continued)

FOREIGN PATENT DOCUMENTS

| | | |
|---|---|---|
| AU | 2003/289742 A1 | 7/2007 |
| CA | 2304396 A1 | 4/1999 |
| CA | 2315309 | 2/2001 |
| CA | 2490342 A1 | 12/2003 |
| DE | 19853033 | 5/2000 |
| EP | 52874 A1 | 6/1982 |
| EP | 225160 | 6/1987 |
| EP | 314095 A1 | 5/1989 |
| EP | 430200 | 6/1991 |
| EP | 547932 A1 | 6/1993 |

(Continued)

OTHER PUBLICATIONS

Whirlpool Co. V. Camco on. 2 S.C.R. 1067 2000.
Glaxosmithkline Inc. V. Apotex Inc. F.C.T 687 2003.
Blajchman, M. A., Transfusion Clinique Et Biologique, "Novel Platelet Products, Substitutes and Alternatives" 2001 8(3) :267-271.
Porter, et al Biochemical and Biophysical Research Communications Growth Inhibition by Methionine Analog Inhibitors of S-Adenosylmethionine Biosynthesis in the Absence of Polyamine Depletion 1984 122 1 350-357.
English Translation of Krylov, Yu F., Chief Editor—Enziklopedia (Continued)

*Primary Examiner* — Karlheinz R Skowronek
*Assistant Examiner* — Roy Teller
(74) *Attorney, Agent, or Firm* — Jianjie Hu

(57) ABSTRACT

The invention relates to chemically as well as physically stable compositions comprising Factor VII or a Factor VII-related polypeptide such that these compositions can be stored, handled and used at room temperature.

28 Claims, 2 Drawing Sheets
(2 of 2 Drawing Sheet(s) Filed in Color)

(56) References Cited

U.S. PATENT DOCUMENTS

| | | | |
|---|---|---|---|
| 6,908,610 B1 | 6/2005 | Sato | |
| 7,015,194 B2 | 3/2006 | Kjalke | |
| 7,078,479 B2 | 7/2006 | Rojkjaer | |
| 7,125,846 B2 | 10/2006 | Rojkjaer | |
| 7,173,000 B2 | 2/2007 | Ruf et al. | |
| 8,022,031 B2 | 9/2011 | Hansen et al. | |
| 8,026,214 B2 | 9/2011 | Jensen et al. | |
| 8,299,029 B2* | 10/2012 | Jensen et al. | 514/14.3 |
| 8,318,904 B2 | 11/2012 | Jensen et al. | |
| 2001/0031721 A1 | 10/2001 | Webb et al. | |
| 2002/0110552 A1 | 8/2002 | Romisch et al. | |
| 2002/0115590 A1 | 8/2002 | Johannessen et al. | |
| 2003/0109446 A1 | 6/2003 | Rojkjaer | |
| 2004/0009918 A1* | 1/2004 | Nedergaard et al. | 514/12 |
| 2004/0037893 A1 | 2/2004 | Hansen et al. | |
| 2004/0043933 A1* | 3/2004 | Hansen et al. | 514/12 |
| 2004/0147439 A1 | 7/2004 | Araki et al. | |
| 2005/0266006 A1 | 12/2005 | Rojkjaer | |
| 2006/0009376 A1 | 1/2006 | Eibl | |
| 2006/0013812 A1 | 1/2006 | Rojkjaer | |
| 2006/0063714 A1 | 3/2006 | Jensen et al. | |
| 2006/0160720 A1 | 7/2006 | Jensen et al. | |
| 2006/0166882 A1 | 7/2006 | Jensen et al. | |
| 2007/0049523 A1 | 3/2007 | Hansen et al. | |
| 2008/0206225 A1 | 8/2008 | Arentsen et al. | |
| 2009/0075895 A1 | 3/2009 | Nedergaard et al. | |
| 2009/0181895 A1 | 7/2009 | Hansen et al. | |
| 2010/0136622 A1 | 6/2010 | Krarup et al. | |
| 2010/0166730 A1 | 7/2010 | Jensen et al. | |

FOREIGN PATENT DOCUMENTS

| | | |
|---|---|---|
| EP | 765669 A1 | 4/1997 |
| EP | 770625 A2 | 5/1997 |
| EP | 872487 A2 | 10/1998 |
| EP | 952215 | 10/1999 |
| EP | 1232753 A1 | 8/2002 |
| JP | 62-195335 A | 8/1987 |
| JP | 3155797 | 7/1991 |
| JP | 6-504678 T | 6/1994 |
| JP | 8/509745 | 10/1996 |
| JP | 11500408 | 1/1999 |
| JP | 00-513720 | 10/2000 |
| JP | 2000-302689 | 10/2000 |
| JP | 2001515460 | 9/2001 |
| JP | 2003-507388 A | 2/2003 |
| JP | 2003-531862 A | 10/2003 |
| NZ | 336548 | 9/2001 |
| WO | 88/00210 A1 | 1/1988 |
| WO | 91/10439 A1 | 7/1991 |
| WO | 92/15686 | 9/1992 |
| WO | 93/00807 A1 | 1/1993 |
| WO | 94/05692 A1 | 3/1994 |
| WO | 94/22905 A1 | 10/1994 |
| WO | 94/26286 A1 | 11/1994 |
| WO | 94/27631 | 12/1994 |
| WO | 95/28954 A1 | 11/1995 |
| WO | 96/12800 | 5/1996 |
| WO | 97/14430 | 4/1997 |
| WO | 97/19687 | 6/1997 |
| WO | 97/26909 A1 | 7/1997 |
| WO | 97/47651 | 12/1997 |
| WO | 98/12225 | 3/1998 |
| WO | 98/22619 A1 | 5/1998 |
| WO | 98/48822 A1 | 11/1998 |
| WO | 99/02160 | 1/1999 |
| WO | 99/49880 | 10/1999 |
| WO | 99/66031 A2 | 12/1999 |
| WO | 00/20835 A2 | 4/2000 |
| WO | 00/48635 A1 | 8/2000 |
| WO | 00/72873 | 12/2000 |
| WO | 01/03726 A1 | 1/2001 |
| WO | 01/12653 A1 | 2/2001 |
| WO | 01/17542 A1 | 3/2001 |
| WO | 01/17567 | 3/2001 |
| WO | 01/17569 | 3/2001 |
| WO | 01/58935 A2 | 8/2001 |
| WO | 01/82943 A2 | 11/2001 |
| WO | 01/83725 A1 | 11/2001 |
| WO | 01/85198 A1 | 11/2001 |
| WO | 01/85199 A1 | 11/2001 |
| WO | 02/17957 | 3/2002 |
| WO | 02/22776 A2 | 3/2002 |
| WO | 03/002524 | 1/2003 |
| WO | 03/006054 A1 | 1/2003 |
| WO | 03/007868 A1 | 1/2003 |
| WO | 03/055511 A1 | 7/2003 |
| WO | 03/055512 A1 | 7/2003 |
| WO | 03/092731 A1 | 11/2003 |
| WO | 2004/000347 A1 | 12/2003 |
| WO | 204/008635 A1 | 1/2004 |
| WO | 2004/048635 A1 | 6/2004 |
| WO | 2004/082708 | 9/2004 |
| WO | 2004/110469 | 12/2004 |
| WO | 2005/058283 | 6/2005 |
| WO | 2006/114448 A2 | 11/2006 |

OTHER PUBLICATIONS

Lekarstv. M., (Encyclopaedia of Medicines/Drugs) RLS-2001, 468; Encyclopedia of Drugs, pp. 468.

Novo Nordisk A/S—Novoseven(R) Coagulation Factor Viia (Recombinant) Package Insert.

PCT/DK03/00419 International search report International Search Report for PCT/DK03/00419, Actual Completion date Oct. 1, 2003.

PCT/DK2004/000181 International search report International Search Report for PCT/DK2004/000181, Actual Completion date Jan. 28, 2005.

Wang, et al., Journal of Parenteral Science & Technology, "Parenteral Formulations of Proteins and Peptides: Stability and Stabilizers", 1988, vol. 42, Issue 10, pp. 4-26.

Wang, 2000, International Journal of Pharmaceutics Lyophilization and Development of Solid Protein Pharmaceuticals, 203—1-60.

Wells, J. A. Biochemistry Additivity of Mutational Effects in Proteins 1990 29 37 8509-8517.

Bach, Ronald et al., "Immunoaffinity Purification of Bovine Factor VII", Blood, vol. 63, Part 2, pp. 393-398 (1984).

Bajaj, S. Paul et al, "Isolation and Characterization of Human Factor VII", Journal of Biological Chemistry, vol. 256, Part1, pp. 253-259 (1981).

Broze, Jr., George J. et al., "Purification and properties of Human COagulation Factor VII", Journal of Biological Chemistry, vol. 255, Part 4, pp. 1242-1247 (1980).

Dike et al., "A Factor VII Concentrate for Therapeutic Use", British Journal of Haematology, vol. 45 pp. 107-118 (1980).

Dombrose et al., "Evidence for Multiple Molecular Forms of Autoprothrombin C (Factor XA)", Thrombosis Research, vol. 3, pp. 737-743 (1973).

English language abstract for JP8508745, published Oct. 15, 1996 (Pharmacia & Upjohn).

Husi, Holger et al, "Separation of Human Vitamin K-Dependent Coagulation Proteins Using Hydrophobic Interaction Chromatogrpahy", Journal of Chromatography, vol. 736, pp. 77-88 (1999).

International Search Report Mailed Jul. 22, 2004 for Pct/Dk2004/000183.

Jesty, Jolyon et al, "Purification of Factor VII From Bovine Plasma", Journal of Biological Checmistry, vol. 249, Part 2, pp. 509-515 (1974).

Klausen, N.K. et al., Analysis of the Glycoforms of human recombinant factor VIIa by capillary electrophoresis and high-performance liquid chromatography, Journal of Chromatography, vol. 718, pp. 195-202 (1995).

Krarup, J.C. et al., "Studies on Coagulation Factor VIIA . . . " Abstracts of Papers—American Chemical Society, vol. 255 (1-2), pp. 201-202, Abstract#: BIO333 (2003).

(56) References Cited

OTHER PUBLICATIONS

Liebman, Howard A. et al., "Immunoaffinity Purification of Factor IX (Christmas Factor) by Using Conformation-Specific Antibodies Directed Against the Factor IX-Metal Complex", Proceedings of the National Academy of Sciences of the USA, vol. 82, pp. 3879-3883 (1985).

Nemerson, Yale et al, "Activation of Proteolytic System by a Membrane Lipoprotein: Mechanism of Action of Tissue Factor", Proceedings of the National Academy of Sciences of the USA, vol. 70, Part 2, pp. 310-314 (1973).

O'Brien, Donogh P. et al, "Purification and Characterization of Factor VII 304-GLN: A Variant Molecule with Reduced Activity Isolated From A Clinically Unaffected Male", Blood, vol. 78, Part 1, pp. 132-140 (1991).

Rao, L.V.M. et al, "Purification of Human Factor VII Utilizing O-(Diethylaminoethyl)-Sephadex and Sulfopropyl-Sephadex Chromatography", Analytical Biochemistry, vol. 136, Part 2, pp. 357-361 (1984).

Ruiz, Sonia M., et al, "Expression and Purification of Recombinant Rabbit Factor VII", Thrombosis Research, vol. 98, pp. 203-211 (2000).

Tomokiyo, K. et al., Large-scale production and properties of human plasma-derived activated Factor VII concentrate, Vox Sanguinis, vol. 84, pp. 54-64 (2003).

Yan, S. Betty, "Review of Conformation-Specific Affinity Purifcation Methods for Plasma Vitamin K-Dependent Proteins", Journal of Molecular Recognition, vol. 9 pp. 211-218 (1996).

EP 765669 English Abstract Apr. 2, 1997, previously cited.

JP 3-155797 English Abstract, Mar. 7, 1991, previously cited.

JP 8-509745 English Language Machine Translation, published Oct. 15, 1996, previously cited.

JP 62-195335 English Abstract, Mar. 9, 2010, previously cited.

JP 2000-513720 English Language Machine Translation, published Oct. 17, 2000 (Novo Nordisk A/S), previously cited.

Brozovic et al., "Stability of Prothrombin and Factor VII in Freeze-Dried Plasma", J. Clin. Path., 1971, vol. 24, pp. 690-693.

Enziklopedia lekarstv. M., RLS-2001, 468; Encyclopedia of drugs, p. 468.

Laegemiddel Kataloget (The Medicine Catalogue), pp. 893-894 (2000) and English translation.

English language machine translation for JP11500408, published Jan. 12, 1999 (ZymoGenetics and Novo Nordisk A/S).

English language abstract for JP6504678, published Jun. 2, 1994 (ZymoGenetics and Novo Nordisk A/S).

English language abstract for JP62195335, published Aug. 28, 1987 (Novo Industri A/S).

Shapiro et al, Thrombosis and Haemostasis Prospective, Randomised Trial of Two Doses . . . 1998 80—773-778.

Moscardó, F. et al. British Journal of Haematology, "Successful Treatment of Severe Intra-Abdominal Bleeding Associated With Disseminated Intravascular Coagulation Using Recombinant Activated Factor VII", 2001 113 1 174-176.

Cooper, A. J. L. Annual Review of Biochemistry Biochemistry of Sulfur Containing Amino Acids 1983 52—187-222.

Cleland, J.L et al. Critial Reviews in Therapeutic Drug Carrier Systems the Development of Stable Protein . . . 1993 10 4 307-377.

Manning, M.C et al. Pharmaceutical Research Stability of Protein Pharmaceuticals 1989 6 11 903-918.

Sichler et al., 2002, "Crystal Structures of Uninhibited Factor VIIa Link its Cofactor and Substrate-Assisted Activation to Specific Interactions", Journal Molecular Biology, 322(3):591-603.

Novo Nordisk, 1999, "NovoSeven Coagulation Factor VIIA (Recombinant),"FDA Article Online pp. 1-24.

PCT/DK2004/000359 International Search Report dated Oct. 1, 2004.

Head et al.,1997, Thrombosis Research, vol. 85, No. 4, pp. 327-329.

Marmur, J., Thrombosis, Hemostasis, and Blood Clotting, Downloading Dec. 13, 2010.

English Translation of Krylov, Yu F., Chief Editor—Enziklopedia Lekarstv. M., (Encyclopaedia of Medicines/Drugs) RLS-2001, 468; Encyclopedia of Drugs, pp. 468, (3 pages total including the book cover & Source information sheet).

Definition of analog from http://cancerweb.ncl.ac.uk/omd/about.html, pp. 1-5. Accessed Jul. 7, 2005.

Factor VII sequence from MCBI, AAA51983, pp. 1-2. Accessed May 17, 2012.

Rudinger J, "Characteristics of the amino acids as components of a peptide hormone sequence", Peptide Hormones, JA Parsons Edition, University Park Press, Jun. 1976, pp. 1-7.

"Designing Custom Peptides", from SIGMA Genosys, pp. 1-2. Acessed Dec. 16, 2004.

Schinzel R, Drueckes P, "The Phosphate recognition site of *Escherichia coli* maltodextrin phosphorylase", FEBS, Jul. 1991, 286 (1,2): 125-128.

Berendsen HJC, "A Glimpse of the Holy Grail?" Science, 1998, 282:642-643.

Voet D, Voet JG, Biochemistry. Second Edition, John Wiley & Sons, Inc., 1995, pp. 235-241.

Ngo JT, Marks J, Karplus M, "Comoutational Complexity, Protein Structure Prediction, and the Levinthal Paradox", The Protein Folding Problem and Tertiary Structure Prediction, K. Merc Jr. and S. Le Garnd Edition, 1994, pp. 491-495.

Bradley CM, Barrick D, "Limits of Copperativity in a Structurally Modular Protein: Response of the Notch Ankyrin Domain to Analogous Alanine Substitutions in Each Repeat", J. Mol. Biol., 2002, 324:373-386.

Horioka et al, Injection-Its Basics, Preparation and Application, 1st Edition, Mar. 22, 1995, Publiushed by Nanzandou, p. 19-23.

Iyakuhin Tenkabutsu Jiten(Pharmaceutical Excipients Dictionary) 2000, Edited by International Pharmaceutical Excipients Council Japan, 1st Edition, Apr. 28, 2000, Published by Yakuji Nippo Ltd, p. 281.

Ammonium Sulfate Precipitation, http://en.wikipedia.org/w/index.php?Title=ammonium_sulfate_precipitation&oldid=440160162, From Wikipedia, the free encyclopedia, 2012.

Hofmeister Series, http://en.wikipedia.org/w/index.php?title=hofmeister_series&oldid=502630992, From Wikipedia, Üle fres encyclopedia, 2012.

Akers et al., Peptides and Proteins as Parenteral Solutions, Pharmaceutical Formulation Development of Peptides and Proteins, 2000, pp. 145-158.

Bedu-Addo et al., Preformulation Development of Recombinant Pegylated Staphylokinase SY161 Using Statistical Design, AAPS PharmSci, 2002, vol. 4, No. 4, pp. 1-13.

Chen et al., Stabilization of Recombinant Human Keratinocyte Growth Factor by Osmolytes and Salts, Journal of Phanvaceutical Sciences, 1996, vol. 85, No. 4, pp. 419-422.

Wang, Yu-Chang John et al, Parenteral Formulations of Proteins and Peptides: Stability and Stabilizers, J Parenter SCI Technol, 1988, vol. 42, pp. S2-S26.

Tubek et al., "Role of Zinc in Hemostasis: A Review," Biol Trace Elem Res, 2008, vol. 121, pp. 1-8.

* cited by examiner

STABILISED SOLID COMPOSITIONS OF FACTOR VII POLYPEPTIDES

CROSS-REFERENCE TO RELATED APPLICATIONS

This application is a continuation of copending U.S. application Ser. No. 11/526,503, filed Sep. 25, 2006, which is a continuation of U.S. application Ser. No. 10/609,780, filed Jun. 30, 2003 (now abandoned), which is a continuation of International Application No. PCT/DK03/00419, filed Jun. 20, 2003, and claims priority under 35 U.S.C. 119 of Danish Application No. PA 2002 00963, filed Jun. 21, 2002 and U.S. Application No. 60/394,153 filed Jul. 3, 2002, and, the contents of which are fully incorporated herein by reference.

FIELD OF INVENTION

The present invention relates to chemically as well as physically stable compositions comprising Factor VII or a Factor VII-related polypeptide such that these compositions can be stored, handled and used at room temperature.

BACKGROUND OF THE INVENTION

Factor VII is a polypeptide involved in the blood clotting process. Today, Factor VIIa can be made by recombinant techniques (rFVIIa) and is widely used as a pro-haemostatic agent. Factor VII (human wild-type) has been described in U.S. Pat. No. 4,784,950. rFVIIa offers today a rapid and highly effective pro-haemostatic response in haemophilic individuals experiencing bleeding. Advantageously, rFVIIa can be used for treating haemophilic individuals that cannot be treated with other coagulation factor products due to antibody formation. Also individuals suffering from Factor VII deficiency or individuals having a normal coagulation system but still experiencing excessive bleeding can be treated successfully with rFVIIa.

Several parameters need to be considered when developing a medicament comprising a polypeptide such as, e.g., Factor VIIa. By example, the medicament needs to be effective, safe and lead to good patient compliance. Moreover, the medicament may be formulated for parenteral administration using pharmaceutically acceptable excipients, which will have to meet with the approval of various world-wide medical regulatory agencies. For the purpose of parenteral administration, it is highly desirable that the formulation is approximately isotonic and that the pH of the formulation is in a physiologically suitable range upon injection/infusion, otherwise it may result in pain and discomfort for the patient. For a general review of protein formulations, see, for example, Cleland et al.: The development of stable protein formulations: A closer look at protein aggregation, deamidation and oxidation, Critical Reviews in Therapeutic Drug Carrier Systems 1993, 10(4): 307-377; and Wang et al., Parenteral formulations of proteins and peptides: Stability and stabilizers, Journal of Parenteral Science and Technology 1988 (Supplement), 42 (2S).

However, for medicaments comprising polypeptides the safety may directly be related to the physical and chemical stability of the polypeptide. Being a polypeptide, Factor VII or a Factor VII-related polypeptide is susceptible to physical degradation, including denaturation and aggregation such as the formation of soluble or insoluble aggregates in the form of dimers, oligomers and polymers, or to chemical degradation, including for example, hydrolysis, deamidation and oxidation. Consequently, the said physical and chemical instability may lead to loss of activity of the Factor VII polypeptide, formation of toxic and immunogenic degradation products, serious risk of introducing thrombosis upon injection of the degraded Factor VII polypeptides, clogging of needles used for injections and risk of non-homogeneity, to name just a few.

Thus, it is essential to provide compositions comprising Factor VII polypeptides that is stabilised against physical and chemical degradation.

Today, recombinantly-made FVII polypeptide is provided as freeze-dried product that is meant to be stored at temperatures between about 2 and about 8° C. The requirement of cooled conditions causes a burden to and is inconvenient for the manufacturer or provider as well as the end user (the patient).

The actual recombinantly-made FVII product is NovoSeven® (Novo Nordisk A/S, Denmark) that consists of 1.2 mg recombinant human Factor VIIa, 5.84 mg NaCl, 2.94 mg $CaCl_2$, $2 H_2O$, 2.64 mg Glycylglycine, 0.14 mg polysorbate 80 and 60.0 mg mannitol. When reconstituted by 2.0 ml of water for injection (WFI), the pH is 5.5 and the thus prepared FVII-containing solution is sufficiently stable for 24 hours at room temperature.

The present investigators have found that upon storage of the lyophilised NovoSeven® product for 6 months at 25° C. about 6 to 7% w/w of the initial content of the rFVIIa is present in the form of aggregates.

Thus, compositions comprising Factor VII polypeptides need to be stabilised so as allowing storage and handling at ambient temperatures. However, the instability of polypeptides relates to several parameters and it is impossible to predict the proper manner of stabilising a Factor VIIa or a Factor VII-related polypeptide.

One approach of stabilising a protein relates to removal of water from the protein, e.g. such as providing the protein in the form of a lyophilised cake, the final matter obtained in a freeze-drying process. However, the freeze-drying process itself is also harmful to proteins; during freeze-drying, the protein solution is first cooled until adequately frozen and bulk water in the protein solution will form ice at this stage. The protein is hereby prone to freeze-induced stress resulting in deformation and precipitation. In the next step, the so-called primary drying stage, the ice sublimes and in the secondary drying stage, adsorbed or bound water is removed under elevated temperatures. During this water removal, the proteins may loose their proper conformation that is provided mainly through hydrogen bonding.

Therefore, to preserve protein conformation, activity and stability during freeze-drying, the polypeptide solution needs to be supplemented with sufficient amounts of proper excipients with cryoprotectant and/or lyoprotectant properties so as to protect the protein from freeze-induced stress and/or stress during removal of water, respectively.

Additionally, when providing a lyophilised product, an essential feature relates to the properties of the lyophilised cake. It needs to have good properties as to its form and structure, i.e. it should not collapse in that such collapsed cakes can be hard or even impossible to dissolve (reconstitute) before use. Conversely, the physical structure of the lyophilised cake may not be too loosen and soft. Therefore, one or more so-called bulking agents are added to the protein solution before freeze-drying.

Other publications of interest regarding stabilisation of polypeptides are as follows:

U.S. 20010031721 A1 (American Home Products) concerns highly concentrated, lyophilised, and liquid Factor IX formulations.

WO 97/26909 (Genetics Institute) concerns lyophilised preparations of Factor IX suitable for storage and administration. The preparations may comprise sucrose or mannitol as a cryoprotectant.

WO 95/28954 (Genetics Institute) concerns preparations of Factor IX suitable for storage and administration. The preparations may comprise sucrose as a cryoprotectant.

It is an objective of the present invention to provide stable compositions of Factor VII polypeptides, substantially without the presence of degradation products and without decreased activity of the Factor VII polypeptides, preferable after prolonged storage at ambient conditions, e.g. for at least 6 months. Furthermore, it is an objective that the stable compositions are suitable for parenteral administration so as not to cause any inconvenience for the patient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1A:
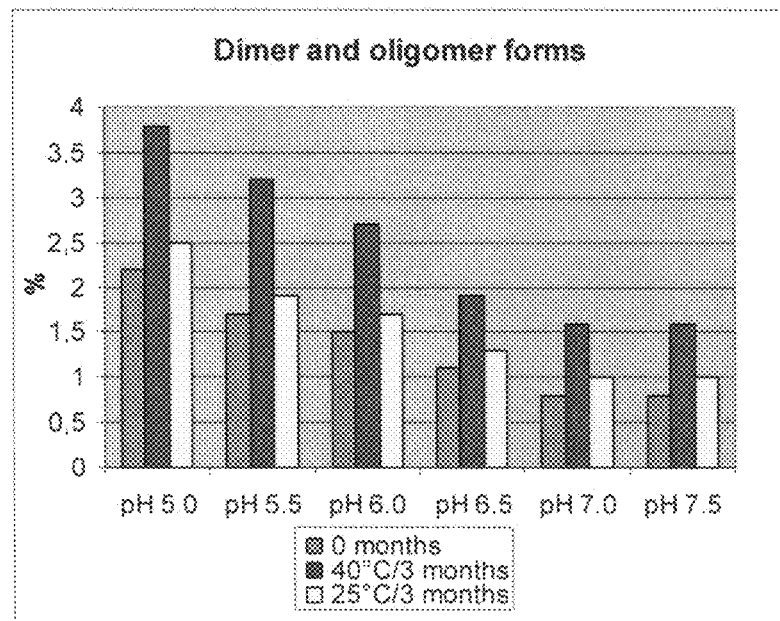
FIGS. 1A and 1B show the stability of the six formulations that were tested as described in Example 11.

It has been found by the present investigators that Factor VII polypeptides can be provided in a composition that is sufficient stable so as to allow for storage at room temperature for about at least 8 months. The investigators have found that the stabilisation relates to the proper combining of some pharmaceutically acceptable excipients.

Accordingly, the present invention relates in a first aspect to stabilised compositions that have a moisture content of not more than about 3% and comprises a Factor VII polypeptide and at least one stability agent selected from the group consisting of a) to e):
  a) a combination of an antioxidant and mannitol;
  b) a combination of methionine and a polyol;
  c) a combination of a saccharide and mannitol;
  d) a combination of sucrose and a polyol; and
  e) methionine.

In a further aspect, the invention relates to a method of preparing a stable Factor VII polypeptide comprising the steps of:
  i) Providing said Factor VII polypeptide in a solution comprising at least one stability agent selected from the group consisting of a) to e):
  a) a combination of an antioxidant and mannitol;
  b) a combination of methionine and a polyol;
  c) a combination of a saccharide and mannitol;
  d) a combination of sucrose and a polyol; and
  e) methionine;
  ii) Processing said solution so as to obtain a solid composition with a moisture content of not more than about 3% w/w.

As mentioned, stabilised Factor VII polypeptides are requested so as to minimise the risk of adverse events and to improve safety and efficacy when administering Factor VII polypeptides for therapeutic purposes. Therefore, a still further aspect of the invention relates to the use of Factor VII polypeptide for the preparation of a medicament for treating a Factor VII-responsive syndrome, said medicament comprising a composition comprising;
  a Factor VII polypeptide and a at least one stability agent selected from the group consisting of
  a) a combination of an antioxidant and mannitol;
  b) a combination of methionine and a polyol;
  c) a combination of a saccharide and mannitol;
  d) a combination of sucrose and a polyol; and
  e) methionine,
said composition having a moisture content of not more than about 3%.

Finally, the invention relates to administering said Factor VII polypeptides for treating a Factor VII-responsive syndrome comprising administering to a subject in need thereof an effective amount of a composition comprising a Factor VII polypeptide and at least one stability agent selected from the group consisting of
  a) a combination of an antioxidant and mannitol;
  b) a combination of methionine and a polyol;
  c) a combination of a saccharide and mannitol;
  d) a combination of sucrose and a polyol; and
  e) methionine;
said composition having a moisture content of not more than about 3%.

DETAILED DESCRIPTION OF THE INVENTION

The present invention relates to storage-stable compositions comprising Factor VII polypeptides. The compositions can be stored at room temperature for an extended period of time without causing substantial degradation of the Factor VII polypeptide. By room temperature is meant the ambient temperature inside a room; it normally ranges from about 5° C. to about 40° C., such as from about 10° C. to 30° C., or 15° C. to 25° C.

By proper predetermined combination of particular pharmaceutically acceptable excipients, the present investigators have provided stabilised compositions comprising Factor VII polypeptides, thus allowing the compositions to be stored at room temperature for an extended period of time such as at least about 8 months. Advantageously, the stabilised compositions need not to be stored at cooled conditions, such as between 2 and 8° C.

The present invention also concerns storage-stable compositions that are stable for at least about 8 months upon storage at about 30° C. The composition is preferably stored in the dark. Thus, the present invention makes it possible to store such compositions at room temperature without increasing the risk of adverse events to the patient administering such compositions. Advantageously, the improved storage-stability will also result in reduced cost in that no special cooled conditions are required upon storage, further resulting in more convenient handling of the composition by the user.

The term "Factor VII polypeptide" is denoted to mean any Factor VII polypeptide that is effective in preventing or treating bleeding. This includes Factor VII polypeptides derived from blood or plasma, or produced by recombinant means.

As used herein, "Factor VII polypeptide" encompasses, without limitation, Factor VII, as well as Factor VII-related polypeptides. The term "Factor VII" is intended to encompass, without limitation, polypeptides having the amino acid sequence 1-406 of wild-type human Factor VII (as disclosed in U.S. Pat. No. 4,784,950), as well as wild-type Factor VII derived from other species, such as, e.g., bovine, porcine, canine, murine, and salmon, said Factor VII derived from blood or plasma, or produced by recombinant means. It further encompasses natural allelic variations of Factor VII that may exist and occur from one individual to another. Also, the degree and location of glycosylation or other post-translation modifications may vary depending on the chosen host cells and the nature of the host cellular environment. The term "Factor VII" is also intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

As mentioned, the term "Factor VII polypeptides" is also denoted to mean "Factor VII-related polypeptides" The term "Factor VII-related polypeptides" are intended to encompass such polypeptides in their uncleaved (zymogen) form, as well as those that have been proteolytically processed to yield their respective bioactive forms. As used herein, "Factor VII-related polypeptides" encompass, without limitation, polypeptides exhibiting substantially the same or improved biological activity relative to wild-type human Factor VII. These polypeptides include, without limitation, Factor VII or Factor VIIa that has been chemically modified and Factor VII variants into which specific amino acid sequence alterations have been introduced that slightly modify or improve the biological activity of the polypeptide.

Moreover, Factor VII-related polypeptides, including variants of Factor VII exhibiting substantially the same or better biological activity than wild-type Factor VII, include without limitation polypeptides having an amino acid sequence that differs from the sequence of wild-type Factor VII by insertion, deletion, or substitution of one or more amino acids.

Factor VII-related polypeptides, including variants, having substantially the same or improved biological activity relative to wild-type Factor VIIa encompass those that exhibit at least about 25%, preferably at least about 50%, more preferably at least about 75%, more preferably at least about 100%, more preferably at least about 110%, more preferably at least about 120%, and most preferably at least about 130% of the specific activity of wild-type Factor VIIa that has been produced in the same cell type, when tested in one or more of a clotting assay, proteolysis assay, or TF binding assay as described in the present specification.

In some embodiments the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see Example 9, below); in other embodiments, the ratio is at least about 2.0; in further embodiments, the ratio is at least about 4.0. In some embodiments of the invention, the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Proteolysis Assay" (see Example 9, below); in other embodiments, the ratio is at least about 2.0; in further embodiments, the ratio is at least about 4.0; in further embodiments, the ratio is at least about 8.0.

Non-limiting examples of Factor VII variants having substantially the same or improved biological activity as wild-type Factor VII include S52A-FVII, S60A-FVII (Lino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota); FVII variants as disclosed in WO 01/58935 (Maxygen ApS); FVII variants having increased biological activity compared to wild-type FVIIa as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVIIa variants with enhanced activity as disclosed in JP 2001061479 (Chemo-Sero-Therapeutic Res Inst.).

Examples of factor VII or factor VII-related polypeptides include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/L305V/V158D/K337A/S314E-FVII, F374Y/V158D/M298Q/K337A/S314E-FVII, F374Y/V158D/E296V/M298Q/S314E-FVII, F374Y/V158D/E296V/K337A/S314E-FVII, F374Y/V158D/E296V/M298Q/K337A-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298WK337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/M298Q/K337A/V158T/S314E-FVII, F374Y/L305V/E296V/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; FVII having substitutions, additions or deletions in the amino acid sequence from 233Thr to 240Asn, FVII having substitutions, additions or deletions in the amino acid sequence from 304Arg to 329Cys, and FVII having substitutions, deletions, or additions in the amino acid sequence Ile153-Arg223.

For purposes of the invention, biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) Measuring the ability of Factor VIIa or a Factor VIIa-related polypeptide to produce activated Factor X (Factor Xa) in a system comprising TF embedded in a lipid membrane and Factor X. (Persson et al., J. Biol. Chem. 272:19919-19924, 1997);

(ii) Measuring Factor X hydrolysis in an aqueous system ("In Vitro Proteolysis Assay", see Example 12, below);

(iii) Measuring the physical binding of Factor VIIa or a Factor VIIa-related polypeptide to TF using an instrument based on surface plasmon resonance (Persson, FEBS Letts. 413:359-363, 1997); and (iv) Measuring hydrolysis of a synthetic substrate by Factor VIIa and/or a Factor VIIa-related polypeptide ("In Vitro Hydrolysis Assay", see Example 12, below); and (v) Measuring generation of thrombin in a TF-independent in vitro system.

The term "Factor VII biological activity" or "Factor VII activity" is intended to include the ability to generate thrombin; the term also includes the ability to generate thrombin on the surface of activated platelets in the absence of tissue Factor.

Example 12 of the present specification describes in detail assays useful for assaying FVII biological activity.

Moreover, throughout the present specification, the terms below have the following meaning:

The term "stabilising" is intended to encompass minimising the formation of aggregates (insoluble and/or soluble) and/or chemical degradation as well as providing maintenance of pH and proper conformation of the protein during storage or production of the compositions so that substantial retention of biological activity and protein stability is maintained. Moreover, stabilising is also denoted to mean lyoprotection and cryoprotection of the protein during production of the compositions at freeze-drying conditions.

The term "structural stabilisation" or "structural stability" is intended to encompass the ability to form a lyophilised plug or cake with good properties and looks, e.g. such that it does not collapse and is readily dissolved before use.

The term "storage-stable" is intended to define a product that is stabilised upon storage at temperatures between 5° C.-40° C. and remains within pre-selected product specifications for a suitable time period—often several months.

The term "physical stability" of Factor VII polypeptides relates to the formation of insoluble and/or soluble aggregates in the form of dimeric, oligomeric and polymeric forms of Factor VII polypeptides as well as any structural deformation and denaturation of the molecule.

The term "chemical stability" is intended to relate to the formation of any chemical change in the Factor VII polypeptides upon storage in dissolved or solid state at accelerated conditions. By example are hydrolysis, deamidation and oxidation. In particular, the sulphur-containing amino acids are prone to oxidation with the formation of the corresponding sulphoxides.

The term "cryoprotectants" as used herein generally include agents, which provide stability to the protein from freezing-induced stresses. Examples of cryoprotectants include polyols such as, for example, mannitol, and include saccharides such as, for example, sucrose, as well as including surfactants such as, for example, polysorbate, poloxamer or polyethylene glycol, and the like. Cryoprotectants also contribute to the tonicity of the formulations.

The term "lyoprotectant" as used herein includes agents that provide stability to the protein during water removal upon the drying process of the lyophilisation process. For example by maintaining the proper conformation of the protein. Examples of lyoprotectants include saccharides, in particular di- or trisaccharides. Cryoprotectants may also have lyoprotectant effects.

The term "agent suitable for keeping the pH in the range of 3 to 9" encompasses those agents that maintain the solution pH in an acceptable range between 3.0 and 9.0. Typical examples of agents capable of keeping the pH within a range of 3 to 9 are the acid form or salts of citric acid, acetic acid, histidine, malic acid, phosphoric acid, tartaric acid, succinic acid, MES, HEPES, PIPES, imidazole, TRIS, lactic acid, glutaric acid and glycylglycine. It is to be understood that a combination of agents, wherein the combination of agents is suitable for maintaining the pH in the above-described range, may also be used in the present invention.

The term "lyophilised cake" as used herein is denoted to encompass the solid composition obtained upon processing a dissolved or at least a partly dissolved composition under conditions involving at least one step of cooling said dissolved/partly dissolved composition to ice followed by at least one step of vacuum drying.

The term "lyophilization" and "freeze-drying" encompasses a process during which liquid is removed from a dissolved or at least partly dissolved composition under conditions involving at least one step of cooling the dissolved or partly dissolved solution to ice followed by vacuum drying. Lyophilization, or freeze-drying, is the most common process for making solid protein pharmaceuticals. The process consists of two major steps: freezing of a protein solution, and drying of the frozen solid under vacuum. The drying step is further divided into two phases: primary and secondary drying. The primary drying removes the frozen water (sublimation of ice) and the secondary drying removes the non-frozen "bound" water (desorption of water). More detailed analysis of each lyophilization step is provided in, e.g., Wang et al, International Journal of Pharmaceutics 203 (2000): 1-60 (see section 4, page 16 ff.).

Typically, a composition is freeze-dried by filling into vials, freezing on the shelves of the freeze-dryer, after which a vacuum is established and the shelves heated to implement primary drying (or sublimation of ice). Thereafter, secondary drying (or desorption of sorbed water) takes place at a higher temperature until the completion of the process, i.e., where the composition contains a sufficiently low content of moisture (water). Methods for freeze-drying are generally known in the art, see, for example, Wang et al, International Journal of Pharmaceutics 203 (2000): 1-60.

It is within the ordinary skill of the practitioner to optimize the freeze-drying conditions in regard of temperature(s), time(s) at each temperature, and also pressure that is to be used during the process for a specific composition.

The term "moisture content" is meant to encompass water associated with the product, including, without limitation, water in adsorbed form, such as unfrozen water entrapped in or adsorbed to the frozen solute phase and/or associated with the amorphous phase or adsorbed to the crystalline solid. The term "water content" is used interchangeably with "moisture content". The desired residual moisture level (moisture content) is a function of the duration and the temperature of the secondary drying step. Several methods for determining the residual moisture content during lyophilization are known in the art; for example, an electronic hygrometer or a residual gas analyser may be used. Moisture contents of freeze-dried formulations can be determined by several methods known in the art, such as, for example, loss-on-drying, Karl Fischer titration, thermal gravimetric analysis (TGA), gas chromatography (GC), or near IR (see, e.g. Wang et al, International Journal of Pharmaceutics 203 (2000): 1-60). Methods for determining water contents (moisture contents) are also described in both the European and U.S. Pharmacopoeias. For example, determination of water content can be performed by Karl Fischer coulometric titration as described in the U.S. Pharmacopoeia (USP <921, Ic>) or the European Phamacopoeia (EP <2.5.32>).

In brief, the method is as follows:
Determination of Water Content by Coulometric Titration:

The Karl Fischer reaction is used in the coulometric determination of water based upon the quantitative reaction of water with sulphur dioxide and iodine in an anhydrous medium. Iodine is produced electrochemically in the reaction cell by oxidation of iodide. The iodine produced at the anode reacts immediately with the water and the sulphur dioxide contained in the reaction cell. The amount of water in the substance is directly proportional to the quantity of electricity up until the titration end-point. When all of the water in the cell has been consumed, the end-point is reached and thus an excess of iodine appears which is detected electrometrically thus indicating the end-point. The percentage water content present in the substance is then calculated.

Moisture content may be defined in terms of the weight of the sample in the vial at the time of analysis (i.e. solids plus the water present-called wet weight basis) or it may be defined in terms where it is corrected for the measured water in the sample (i.e. dry weight basis). In case of freeze-dried products with low moisture contents the two measurements (wet weight basis vs. dry weight basis) yield very similar results. As used herein, moisture contents are defined in terms of the solids plus the water present (i.e., wet weight basis).

The term "bulking agent" generally includes agents, which provide good lyophilised cake properties, which form a pharmaceutically elegant product, which help the protein overcome various stresses, shear/freezing for example, associated with lyophilisation processes, and which help to maintain protein activity levels during the freeze-drying process and subsequent storage. Typical examples of bulking agents include mannitol, glycine, sucrose, lactose. These agents may also contribute to the tonicity of the formulations.

The term "tonicity modifier" is denoted to mean any agent capable of adjusting the tonicity of the composition such that upon dissolving the composition at the time of use, the composition has a tonicity within the physiological range of the blood, peritoneal fluid or other relevant body fluids. Obviously, the tonicity may also depend on whether the reconstitution solution comprises tonicity-modifying agents.

The term "surfactants" generally include those agents, which protect the protein from air/solution interface-induced stresses and solution/surface induced-stresses. For example surfactants may protect the protein from aggregation. Suitable surfactants may include e.g. polysorbates, polyoxyethylene alkyl ethers such as Brij 35®, or poloxamer such as Tween 20, Tween 80, or poloxamer 188. Preferred detergents are poloxamers, e.g. Poloxamer 188, Poloxamer 407; polyoxyethylene alkyl ethers, e.g. Brij 35®, Cremophor A25, Sympatens ALM/230; and polysorbates/Tweens, e.g. Polysorbate 20, Polysorbate 80. More preferred are Poloxamers, e.g. Poloxamer 188, and Tweens, e.g. Tween 20 and Tween 80.

The term "initial content" relates to the amount of Factor VII polypeptides added to a composition at the time of preparation. The concentration given herein (mg/ml) refer to either the concentration in the solution of Factor VII polypeptide before removing the moisture (e.g. before freeze-drying) or in the reconstituted composition, or is referred as % w/w, which then relates to the concentration in the solid composition, e.g. the lyophilised cake.

As used herein, amounts specified are understood to be ± about 10%; thus about 50 mM includes 50 mM±5 mM, 4% includes 4%±0.4%, etc.

As stated above, the present investigators have contributed essentially to the art by stabilising Factor VII polypeptides thereby allowing long-term storage without causing increased risk and inconvenience to the user.

The present investigators have found that a number of crucial parameters need to be adjusted in stabilising Factor VII polypeptides. One important parameter relates, at least in part, to the moisture content, e.g. water. The moisture content should be limited. As a further essential parameter, the composition should at least include one stability agent. According to the present invention, a proper stability agent includes the combination of at least two groups of pharmaceutically acceptable excipients selected from the group consisting of antioxidants, saccharides and polyols. The saccharides and polyols have lyoprotectant and/or cryoprotectant properties that may be important, at least in part, in the event where the composition is freeze-dried. In general, improved stability may be achieved, in part, by the proper combination of at least two of these groups of excipients. However, more specifically it was found that when said combination comprises a saccharide (sucrose) or an antioxidant (methionine), the stabilising effect may be even more significant. Moreover, it was also surprisingly found that methionine prevents oxidative degradation of the Factor VII polypeptides.

Hence in a first aspect the invention relates to a composition comprising a Factor VII polypeptide and at least one stability agent selected from the group consisting of
   a) a combination of an antioxidant and mannitol;
   b) a combination of methionine and a polyol;
   c) a combination of a saccharide and mannitol;
   d) a combination of sucrose and a polyol; and
   e) methionine,
said composition having a moisture content of not more than about 3%.

That is to say that one embodiment of the invention comprises a combination of an antioxidant and mannitol; a second embodiment comprises a combination of methionine and a polyol; another embodiment comprises a combination of a saccharide and mannitol; in still another embodiment, the composition comprises a combination of sucrose and a polyol; and finally in another suitable embodiment, the composition comprises methionine.

As stated, the stabilising agent according to the invention includes combining at least two groups of pharmaceutically acceptable excipients. In suitable embodiments thereof, the stabilising agent further comprises a third group of excipients. Hence, in one embodiment, the combination of an antioxidant and mannitol further comprises a saccharide. In a second embodiment thereof, the combination of methionine and a polyol further comprises a saccharide. In still interesting embodiments, the combination of a saccharide and mannitol further comprises an antioxidant and the combination of sucrose and a polyol further comprises an antioxidant. In one embodiment, the composition of the invention comprises mannitol and sucrose; in another embodiment, the composition comprises mannitol, sucrose and methionine; in another embodiment, the composition comprises mannitol and trehalose; in another embodiment, the composition comprises mannitol, trehalose and methionine According to the invention, the Factor VII polypeptide is meant to encompass the polypeptides as described above. In suitable embodiments of the invention, the Factor VII polypeptide is selected from the group consisting of Human Factor VIIa, Recombinant Human Factor VIIa and a Factor VII Sequence Variant. Preferably, the Factor VII Polypeptide is Human Factor VIIa or Recombinant Human Factor VIIa or a Factor VII-related polypeptide wherein the ratio between the activity of said Factor VII-related polypeptide and wild-type Factor VII is at least 1.25 when tested in one or more of the "In Vitro Proteolysis Assay" and the "in Vitro Hydrolysis Assay" as described in the present specification.

As stated, the moisture content should be limited. For the purposes of the present invention, the Factor VII polypeptides, when provided in bulk, may be provided in solid or liquid form. However, typically the Factor VII polypeptides, when provided in bulk, are in liquid form. Thus, further processing of the bulk proteins for the manufacturing of compositions requires the steps of adding suitable excipients and removing the liquid from the bulk, said addition of excipients may be carried out before or after removing the liquid. One such mean for removing liquid from a protein relates to freeze-drying. Therefore, in a preferred embodiment of the present invention, the composition is in the form of a lyophilised cake. However, the present invention does not preclude other processes that are suitable for removing the liquid from the bulk polypeptide so as to achieve a solid composition with moisture content of not more than about 3% w/w.

Moreover, according to the invention, the moisture content is preferably not more than about 2.5% w/w, preferably not more than about 2% w/w, most preferably not more than about 1.5% w/w.

As may be understood, the invention relates, in part, to limiting the degradation of Factor VII polypeptides during preparation, e.g. during admixing of excipients and removing of liquid so as to achieve a solid composition with moisture content of the most 3% w/w, and to limiting said degradation from the time of manufacturing the solid composition until the time of use, e.g. until the time when the composition is to be administered by a patient.

Therefore, as a still further parameter in stabilising compositions comprising Factor VII polypeptides, the pH should be kept in the pH range within 3 to 9 when dissolved in aqueous solvent, such as, e.g., pure water or aqueous buffer. That is to say that the pH in the polypeptide solution at the time before removing the moisture content, e.g. before freeze-drying, should be kept within a pH of about 3 to about 9. Advantageously, this pH range is also within the desired physiological range, thereby causing no harm to the user upon administering the composition by parenteral means. Preferably, the pH of the solution is from about 4.0 to about 9.0, such as 4.0 to 8.0, 4.0 to 7.5, 4.0 to 7.0, 4.5 to 7.0, 4.5 to 6.8, 4.5 to 6.5, 5.0 to 7.0, 5.0 to 6.5, 5.0 to 6.0, 5.5 to 6.5, or about 5.5 to about 6.0 such as about 5.5, 5.6, 5.7, 5.8, 5.9, or 6.0.

Hence, interesting embodiments of the invention further comprises an agent suitable for keeping the pH of said composition in the range of 3 to 9 when dissolved in aqueous solution (e.g. water). Accordingly, in suitable embodiments thereof, the agent suitable for keeping the pH in the range of 3 to 9 is selected from the group consisting of acid or salts of citric acid, acetic acid, histidine, malic acid, phosphoric acid, tartaric acid, succinic acid, MES, HEPES, imidazole, TRIS, lactic acid, glutaric acid, PIPES and glycylglycine.

Furthermore, the suitable agent for keeping the pH in the range of 3 to 9 may also be a mixture of at least two such listed agents, wherein the mixture is able to provide a pH value in the specified range. The concentration of the suitable agents is in the range of from about 0.1 mM to 100 mM; from about 0.2 mM to 50 mM; from about 0.5 mM to 25 mM; from about 1 mM to 20 mM; or from about 1 mM to 10 mM.

As can be seen from Example 5 and 6, the present investigators have provided compositions with low contents of oxidised forms and aggregates upon termination of the manufacturing process, i.e. upon termination of the freeze-drying process, by combining proper amounts of mannitol (a polyol), sucrose (a saccharide) and an antioxidant (methionine). Thus, the compositions according to the invention are characterised by having a low initial content of oxidised forms and aggregates before being subjected to storage.

Degradation of the Factor VII polypeptide by the oxidative pathway as well as by the aggregation pathway are sensitive parameters of stability.

Typically, the compositions are stabilised upon termination of the freeze-drying such that less than 5% w/w, such as less than 4, 3 or 2% w/w of the initial content of Factor VII polypeptide is converted into its oxidised forms. The initial content of said Factor VII polypeptide being the amount added to the composition upon preparation of the composition before the freeze-drying step. Moreover, less than 5% w/w, such as less than 4.0%, 3.0%, 2.5%, 2%, 1.5%, or less than 1% w/w of the initial content of Factor VII polypeptide is recovered as aggregate forms, as determined by conventional analytical methods (such as, for example, as described in the Examples of the present application).

The present investigators have found that further degradation (i.e., as calculated from the time of termination of the manufacturing process until 8 months of storage at 30° C.) of a Factor VII polypeptide is minimal upon storage under ambient conditions. As can be seen from Example 5, upon storage at 30° C. for 8 months the increase is such that less than 10% w/w of the initial content of Factor VII polypeptides is recovered as oxidised forms of Factor VII polypeptides in addition to the content of said oxidised forms present at the time of termination freeze-drying. Of great importance, it was found that compositions comprising an antioxidant (methionine) are more stable towards oxidative degradation of the Factor VII polypeptide.

Therefore, according to the present invention, suitable compositions have a limited increase in the content of oxidised forms upon storage for at least 8 months at ambient conditions. That is to say that in still more interesting embodiments, the composition is stable such that no more than about 6% w/w of the initial content of Factor VII polypeptide is additionally degraded into oxidised forms upon storage of the composition for 8 months at 30° C. after termination of the manufacturing process, e.g. freeze-drying process. In further suitable embodiments thereof, not more than about 5, 4, 3, 2, or 1.5% w/w or of the Factor VII polypeptide is additionally converted into oxidised forms, as calculated from the time of termination of the manufacturing process until 8 months of storage at 30° C. In these embodiments of the invention the compositions are stable such that not more than about 5% (4, 3, 2, or 1.5%) w/w of the initial content of Factor VII polypeptide is converted to oxidised forms upon storage of said composition at 30° C. for 8 months. As stated above, the initial content relates to the amount of Factor VII polypeptide added to the composition upon preparation of the composition before the freeze-drying step.

As indicated, the degradation of Factor VII polypeptides by the aggregation pathway may also be regarded as an essential stability indicating parameter.

The present investigators have found that further degradation (i.e., as calculated from the time of termination of the manufacturing process until 8 months of storage at 30° C.) of a Factor VII polypeptide is minimal upon storage under ambient conditions. As can be seen from Example 6, not more than about 5% w/w, such as not more than about 4, 3, 2.5, 2.0, 1.5, or 1.0% w/w of the content of a Factor VII polypeptide is additionally recovered as aggregates upon storage for 8 months at 30° C. Also of great importance, it was found that compositions comprising a saccharide (sucrose) are more stable towards formation of aggregates.

Thus, interesting embodiments of the invention relate to compositions that are stable such that not more than about 5% w/w of the initial content of Factor VII polypeptide is converted to aggregates upon storage of said composition at 30° C. for 8 months. As stated above the initial content of said Factor VII polypeptide being the amount added to the composition upon preparation of the composition before the freeze-drying step. By proper optimisation of, at least in part, the contents of saccharides, polyols and antioxidants, the composition is stable such that not more than about 4.0%, 3.0% w/w, such as 2.5, 2.0, 1.5, or 1.0% w/w, of the initial content of Factor VII polypeptide is converted to aggregates upon storage of said composition at 30° C. for 8 months.

Thus, advantageously, the compositions of the invention have low contents of oxidised forms and aggregates upon termination of the manufacturing process, i.e. upon termination of the freeze-drying process, and thus the compositions according to the invention are characterised by having a low initial content of oxidised forms and aggregates before being subjected to storage, e.g. not more than about 5% w/w, such as 4%, 3%, or 2% w/w of the initial contents of Factor VII polypeptide is converted into an oxidised form, and less than 5% w/w, such as not more than about 4.0%, 3.0%, 2.5%, 2%, 1.5%, or not more than about 1% w/w, is converted into a dimeric or higher-order polymeric form upon termination of the manufacturing process Moreover and advantageously, the compositions of the invention are storage-stable, e.g. less than 10% w/w, such as 6%, 5%, 4%, 3%, 2%, or 1.5% w/w of the initial contents of Factor VII polypeptide is converted into an oxidised form, and less than 5% w/w, such as 4%, 3%, 2.5%, 2%, 1.5%, or 1% w/w is converted into a dimeric or higher-order polymeric form upon storage at 30° C. for at least 8 months in the dark.

As mentioned, said improved stability relates to the proper combination of particular excipients. According to the present invention, the excipients should be selected from the group of saccharides, polyols and antioxidants in that the saccharides and polyols exhibit lyoprotectant and/or cryoprotectant properties. More specifically, in suitable embodiments according to the invention, the saccharides of interest are di- and tri-saccharides and polysaccharides such that the saccharides may be selected from the group consisting of sucrose, dextrose, lactose, maltose, trehalose, cyclodextrins, maltodextrins and dextrans. Moreover, in some embodiments, the polyol is selected from the group consisting of mannitol, sorbitol and xylitol. In still interesting embodiments, the antioxidant is selected from the group consisting of homocysteine, cysteine, cystathionine, methionine, gluthatione, and peptides containing any one of homocysteine, cysteine, cystathionine, methionine and gluthatione.

It is understood that the saccharide and polyol excipients, respectively, may also be a mixture of at least two such listed agents. In one series of embodiments of the invention, the saccharide excipient used is a combination of at least two di-, tri- and/or polysaccharides, such as, for example, sucrose in combination with cyclodextrin, trehalose in combination with cyclodextrin, sucrose in combination with dextran, or sucrose in combination with lactose. In one series of embodiments of the invention, the polyol excipient used is a combination of at least two polyols, such as, for example, mannitol in combination with sorbitol, mannitol in combination with xylitol, or sorbitol in combination with xylitol. In one series of embodiments of the invention, the antioxidant excipient used is a combination of at least two antioxidants, such as, for example, methionine in combination with one or more of homocysteine, cysteine, cystathionine, gluthatione, and peptides containing any one of homocysteine, cysteine, cystathionine, methionine and gluthatione.

The present investigators have recognised the proper combination of the polyols and the saccharides as well as their content so as, at least in part, to achieve favourable stability.

Hence, in some more interesting embodiments of the invention, the polyols are to be present in an amount ranging from about 5% w/w to about 90% w/w. Preferably, the amount of the polyol is to be present in a range from about 18% w/w to about 88% w/w, such as from about 18% w/w to about 83% w/w, 25% to 80%, 30% to 65%, 30% to 80%, 40% to 80%, 50% to 80%, 30% to 75%, 40% to 75%, 50% to 75%, or from about 50% to about 70% w/w.

The polyol are to be present in an amount ranging from about 0.5 to 75 mg/ml, such as from about 2 to 60 mg/ml, 5 mg/ml to 55 mg/ml, 8 to 45 mg/ml, 10 to 40 mg/ml, 10 to 30 mg/ml, or from about 2 to 45 mg/ml, 5 mg/ml to 45 mg/ml, 5 to 35 mg/ml, 5 to 25 mg/ml, 5 to 20 mg/ml, 20 to 40 mg/ml, or such as from about 20 to 30 mg/ml, Moreover, in interesting embodiments thereof as well as in some other interesting embodiments of the invention, the saccharide is to be present in the composition in an amount ranging from about 0 to about 85% w/w. In further interesting embodiments thereof, the amount ranges from about 3% w/w to about 80% w/w, such as from about 7% w/w to about 75% w/w, 10% to 70%, 10% to 50%, 20% to 50%, 10% to 40%, or from about 10% w/w to about 35% w/w.

The saccharide should be in an amount ranging from about 0.5 to 75 mg/ml, such as from about 2 to 60 mg/ml, from about 5 mg/ml to 55 mg/ml, from about 8 to 45 mg/ml, from about 10 to 40 mg/ml, from about 10 to 30 mg/ml, or from about 2 to 45 mg/ml, from about 5 mg/ml to 45 mg/ml, from about 5 to 35 mg/ml, from about 5 to 25 mg/ml, such as from about 5 to 20 mg/ml.

Moreover, the present investigators have recognised that the proper amounts of antioxidants should range between from about 0.05 to 10 mg/ml, such as from about 0.1 to 5 mg/ml, 0.1 mg/ml to 2.5 mg/ml, 0.1 to 2 mg/ml, or from about 0.1 to 1 mg/ml.

Importantly, the ratio between the polyol and the saccharide needs to be proper adjusted. In suitable embodiments of the invention, said polyol is in a weight ratio relative to said saccharide ranging from about 100:1 to 1:50. In even more suitable embodiments thereof, said weight ratio is from about 50:1 to 1:10, more preferably from about 20:1 to 1:5. In other suitable embodiments, the weight ratio relates to ranges from about 10:1 to 1:2, and from about 6:1 to 1:2. However, as was found out by the present investigators (see Example 5), the lyophilised cake collapsed upon incorporating higher amounts of the saccharides. As such, very suitable embodiments relate to those wherein said sugar alcohol is in a weight ratio relative to said saccharide ranging from about 4:1 to 1:1, such as from about 4:1 to 3:2 or from about 1:1 to 3:2.

In some embodiments of the invention, the polyol is mannitol and in still further embodiments the saccharide is sucrose. Moreover, in still further embodiments the antioxidant is methionine.

The compositions may further be suitable formulated by incorporating other pharmaceutically acceptable excipients so as to achieve compositions acceptable for parenteral administration, in particular to intravenous administration. Actual methods for preparing compositions for parenteral administration will be known or apparent to those skilled in the art and are described in more detail in for example, Remington: The Science and Practice of Pharmacy, 19th ed., Mack Publishing Company, Easton, Pa. (1995). The term "excipients" includes pharmaceutical acceptable reagents to provide good lyophilised cake properties (bulking agents) as well as provide lyoprotection and cryoprotection of the protein, maintenance of pH, maintenance of acceptable tonicity as well as proper conformation of the protein during storage so that substantial retention of biological activity and protein stability is maintained.

Thus, according to the invention, the compositions further comprise a tonicity modifier. The tonicity modifier may be selected from the group consisting of sodium acetate, sodium lactate, sodium chloride, potassium chloride and calcium chloride. However, other suitable tonicity modifiers are not precluded. It is also noted, that compositions may comprise much higher concentrations of the tonicity-modifying agent as long as the composition is made isotonic or close to isotonic prior to use (e.g., slightly hypertonic or hypotonic), for example bulk compositions need not to be isotonic with the physiological range.

Further stabilisation of a composition comprising a Factor VII polypeptide can be obtained by the addition of surfactants. Thus, in still interesting embodiments of the invention, the compositions further comprising a surfactant, the surfactant being selected from the group consisting of polysorbates, e.g. Tween®, such as polysorbate 20 or 80; polyoxyethylene alkyl ethers, e.g., polyoxyl 23 lauryl ether (Brij 35®) or poloxamers, such as poloxamer 188 (e.g. Pluronic®) or poloxamer 407, (e.g., Lutrol®) and other ethylene/polypropylene block polymers, polyethyleneglycols (PEG) such as PEG8000, or Typically, the surfactants are added in an amount of from 0.005 to 5 mg/ml. Preferred amounts are from 0.01 to 3 mg/ml, more preferred from 0.01 to 0.3 mg/ml for Tween 20 and/or Tween 80 and from 0.05 to 3.0 mg/ml for Poloxamer 188.

In still preferred embodiments of the invention, the composition further comprises other pharmaceutical excipients acting as bulking agent. That is to say that bulking agents other than mannitol are included in the compositions. In particular, bulking agents are included in compositions prepared by freeze-drying.

Initial contents of Factor VII polypeptide in the composition is preferably from about 0.6 mg/ml to about 10.0 mg/ml, such as from about 0.6 mg/ml to about 6.0 mg/ml, from about 0.6 mg/ml to about 5 mg/ml, or from about 0.6 mg/ml to about 4 mg/ml.

In one embodiment, the composition comprises: Factor VII polypeptide, Mannitol, Sucrose, and Tween 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In one embodiment, the composition comprises: Factor VII polypeptide, Mannitol, Sucrose, methionine, and Tween 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition comprises Factor VII polypeptide, Mannitol, Sucrose, Histidine, and Tween 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In one embodiment, the composition comprises: Factor VII polypeptide, Mannitol, Sucrose, methionine, Histidine, and Tween 80, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition comprises Factor VII polypeptide, Mannitol, Sucrose, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition comprises Factor VII polypeptide, Mannitol, Sucrose, methionine, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition comprises Factor VII polypeptide, Mannitol, Sucrose, Histidine, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In another embodiment, the composition comprises Factor VII polypeptide, Mannitol, Sucrose, Histidine, methionine, and Poloxamer 188, has a moisture content of not more than about 3%, and has a pH in the range of 5.0 to 7.0 when the composition is dissolved in water. In one embodiment, the composition further comprises one or more components selected from the list of: CaCl2, NaCl, and Glycylglycine. In one embodiment, the Factor VII polypeptide is human Factor VIIa.

In further embodiments, the compositions are as shown in Table A below.

TABLE A

| Compound | Formulation A | Formulation B | Formulation C | Formulation D |
|---|---|---|---|---|
| FVII polypeptide | 0.6 to 10 mg/ml | 0.6 to 10 mg/ml | 0.6 to 10 mg/ml | 0.6 to 10 mg/ml |
| CaCl2 × 2H2O | 5 to 20 mM | 5 to 20 mM | 5 to 20 mM | 5 to 20 mM |
| NaCl | 0-50 mM | 0-50 mM | 0-50 mM | 0-50 mM |
| Glycylglycine | 0-15 mM | 0-15 mM | 0-15 mM | 0-15 mM |
| L-Histidine | 0-20 mM | 0-20 mM | 0-20 mM | 0-20 mM |
| Mannitol | 20 to 40 mg/ml | 20 to 40 mg/ml | 20 to 40 mg/ml | 20 to 40 mg/ml |
| Sucrose | 5 to 20 mg/ml | — | — | 5 to 20 mg/ml |
| Methionine | 0-1 mg/ml | 0-1 mg/ml | 0-1 mg/ml | 0-1 mg/ml |
| Tween 80 | 0.05 to 0.15 mg/ml | 0.05 to 0.15 mg/ml | | |
| Poloxamer 188 | — | — | 0.5-3 mg/ml | 0.5-3 mg/ml |
| pH | 5.0 to 7.0 | 5.0 to 7.0 | 5.0 to 7.0 | 5.0 to 7.0 |

In further embodiments, the compositions are as shown in Table B below

TABLE B

| Compound | Formulation E | Formulation F | Formulation G | Formulation H |
|---|---|---|---|---|
| FVIIa polypeptide | 1.0 mg/ml | 1.0 mg/ml | 1.0 mg/ml | 1.0 mg/ml |
| CaCl2 × 2H2O | 10 mM | 10 mM | 10 mM | 10 mM |
| NaCl | 39 mM | 39 mM | 39 mM | 39 mM |
| Glycylglycine | 10 mM | 10 mM | 10 mM | 10 mM |
| Mannitol | 25 mg/ml | 25 mg/ml | 25 mg/ml | 25 mg/ml |
| Sucrose | 10 mg/ml | 10 mg/ml | 10 mg/ml | 10 mg/ml |
| Methionine | 0.5 mg/ml | 0.5 mg/ml | 0.5 mg/ml | 0.5 mg/ml |
| Tween 80 | 0.1 mg/ml | — | 0.1 mg/ml | — |
| Poloxamer 188 | — | 1.0 mg/ml | — | 1.0 mg/ml |
| L-Histidine | — | — | 10 mM | 10 mM |
| pH | 6.0 | 6.0 | 6.0 | 6.0 |

| Compound | Formulation I | Formulation J | Formulation K | Formulation L |
|---|---|---|---|---|
| FVII polypeptide | 1.0 mg/ml | 1.0 mg/ml | 1.0 mg/ml | 1.0 mg/ml |
| CaCl2 × 2H2O | 10 mM | 10 mM | 10 mM | 10 mM |
| NaCl | 39 mM | 39 mM | 39 mM | 39 mM |
| Glycylglycine | 10 mM | 10 mM | 10 mM | 10 mM |
| Mannitol | 25 mg/ml | 25 mg/ml | 25 mg/ml | 25 mg/ml |
| Sucrose | 10 mg/ml | 10 mg/ml | 10 mg/ml | 10 mg/ml |
| Methionine | — | — | — | — |
| Tween 80 | 0.1 mg/ml | — | 1.0 mg/ml | — |
| Poloxamer 188 | — | 1.0 mg/ml | — | 1.0 mg/ml |
| L-Histidine | — | — | 10 mM | 10 mM |
| pH | 6.0 | 6.0 | 6.0 | 6.0 |

In further embodiments E1-L1, the compositions contains the excipients, and amounts thereof, listed in Table B above, but are formulated at pH 5.9.

In further embodiments E2-L2, the compositions contains excipients, and amounts thereof, as listed in Table B above, but are formulated at pH 5.8.

In further embodiments E3-L3, the compositions contains excipients, and amounts thereof, as listed in Table B above, but are formulated at pH 5 7.

In further embodiments E4-L4, the compositions contains excipients, and amounts thereof, as listed in Table B above, but are formulated at pH 5 6.

In further embodiments E5-L5, the compositions contains excipients, and amounts thereof, as listed in Table B above, but are formulated at pH 5.5.

As discussed above, the present investigators have provided a method for stabilising Factor VII polypeptides by providing the proteins in solid compositions comprising selected pharmaceutically acceptable excipients, of which it is important to include a stabilising agent. According to the invention, such a stabilising agent is composed of a combination of at least two groups of excipients selected from excipients being saccharides, polyols or antioxidants. Moreover, the present investigators have found that saccharides (sucrose) and antioxidants (methionine) are essential for improving the stability of Factor VII polypeptides.

Therefore, a further aspect of the invention relates to a method of preparing a stable Factor VII polypeptide. The method comprises the steps of:
  i) Providing said Factor VII polypeptide in a solution comprising at least one stability agent selected from the group consisting of
    a) a combination of an antioxidant and mannitol;
    b) a combination of methionine and a polyol;
    c) a combination of a saccharide and mannitol;
    d) a combination of sucrose and a polyol; and
    e) methionine
  ii) Processing said solution so as to obtain a solid composition with a moisture content of not more than about 3% w/w.

In particular interesting embodiments thereof, the method comprises that said antioxidant is selected from the group consisting of homocysteine, cysteine, cystathionine, methionine, gluthatione, and peptides containing any one of homocysteine, cysteine, cystathionine, methionine and gluthatione. In a preferred embodiment, the antioxidant is methionine. In still further interesting embodiments, said saccharide is selected from the group consisting of sucrose, dextrose, lactose, maltose, trehalose, cyclodextrins, maltodextrins and dextrans. In preferable embodiments the polyol is mannitol and the saccharide is sucrose. Moreover, in still preferable embodiments thereof, the antioxidant is methionine.

Preferably the content of the saccharide and optionally the content of the antioxidant in said solution i) should be adjusted so as to achieve superior stabilised Factor VII polypeptides.

According to the invention, the saccharide should be in an amount ranging from about 0.5 to 75 mg/ml, such as from about 2 to 60 mg/ml, from about 5 mg/ml to 55 mg/ml, from about 8 to 45 mg/ml, from about 10 to 40 mg/ml, from about 10 to 30 mg/ml, or from about 2 to 45 mg/ml, from about 5 mg/ml to 45 mg/ml, from about 5 to 35 mg/ml, from about 5 to 25 mg/ml, such as from about 5 to 20 mg/ml.

According to the invention, the polyol should be in an amount ranging from about 0.5 to 75 mg/ml, such as from about 2 to 60 mg/ml, from about 5 mg/ml to 55 mg/ml, from about 8 to 45 mg/ml, from about 10 to 40 mg/ml, from about 10 to 30 mg/ml, or from about 2 to 45 mg/ml, from about 5 mg/ml to 45 mg/ml, from about 5 to 35 mg/ml, from about 5 to 25 mg/ml, such as from about 5 to 20 mg/ml.

The antioxidant should be provided in an amount ranging from about 0.05 to 10 mg/ml, preferably from about 0.1 to 5 mg/ml, more preferably from about 0.1 mg/ml to 2.5 mg/ml, even more preferably from about 0.1 to 2 mg/ml, most preferably from about 0.1 to 1 mg/ml.

In a preferred embodiment, the method for preparing a stable Factor VII polypeptide comprises freeze-drying. The freeze-drying relates to a process, wherein the solution comprising said Factor VII polypeptide is filled into lyophilisation vials or the like. Said Factor VII polypeptide may optionally be subjected to sterile filtration before start of freeze-drying. Cooling is applied to the shelves of the freeze-drier in order to freeze the vials and the solution below critical product temperatures. Water is removed by introducing vacuum and condensation of water vapour on the ice-condenser of the freeze-drier. When the product is dry, usually less than 3% residual moisture content (e.g., measured by Karl Fischer coulometric titration as described above), the vials are closed and capped. Manufacturing is finalised and the composition is now in a form of a lyophilised cake.

Such compositions, when administered to a patient by injectable means, need to be reconstituted in a suitable liquid before use. They may also be reconstituted for other purposes, e.g. for reformulation into other pharmaceutical compositions. However, the present invention does not preclude that the compositions may be administered to a patient in their solid form.

The compositions are reconstituted using an acceptable, preferably sterile, diluent or carrier, preferably an aqueous carrier. A variety of aqueous carriers may be used, e.g., water (e.g. Water for Injection/WFI), buffered water, saline (e.g. 0.4% saline), glycine (e.g. 0.3% glycine), histidine, and the like. The reconstitution diluent may also contain one or more salts, such as a calcium salt (e.g. CaCl2) or a combination of a sodium salt and a calcium salt (e.g. NaCl and CaCl2).

The reconstituted compositions are intended for parenteral administration for prophylactic and/or therapeutic treatment. Preferably, the pharmaceutical compositions are administered parenterally, i.e., intravenously, subcutaneously, or intramuscularly, or they are administered by way of continuous or pulsative infusion.

Therefore, a still further aspect of the invention relates to the use of the solid stabilised composition for the preparation of a medicament for treating a Factor VII-responsive syndrome.

That is to say that one aspect of the invention relates to the use of Factor VII polypeptide for the preparation of a medicament for treating a Factor VII-responsive syndrome, said medicament comprising a composition comprising;
a Factor VII polypeptide and a at least one stability agent selected from the group consisting of
 a) a combination of an antioxidant and mannitol;
 b) a combination of methionine and a polyol;
 c) a combination of a saccharide and mannitol;
 d) a combination of sucrose and a polyol; and
 e) methionine,
said composition having a moisture content of not more than about 3%.

Furthermore, in another aspect the invention relates to administering said stabilised Factor VII polypeptide to a patient for treating a Factor VII-responsive syndrome. Thus, the invention relates to a method of treating a Factor VII-responsive syndrome comprising administering to a subject in need thereof an effective amount of a composition comprising a Factor VII polypeptide, and at least one stability agent selected from the group consisting of
 a) a combination of an antioxidant and mannitol;
 b) a combination of methionine and a polyol;
 c) a combination of a saccharide and mannitol;
 d) a combination of sucrose and a polyol; and
 e) methionine;
said composition having a moisture content of not more than about 3%.

In different embodiments, said Factor VII-responsive syndrome is haemophilia A, haemophilia B, Factor XI deficiency, Factor VII deficiency, thrombocytopenia, von Willebrand's disease, presence of a clotting Factor inhibitor, surgery or trauma. Additionally, Factor VII-responsive syndrome may be associated with anticoagulant therapy.

As stated the composition is in solid form. Accordingly, in a suitable embodiment the medicament should be suitable for being dissolved, which allows for parenteral administration of the medicament. Thus, when administering the compositions to a patient, it comprises the step of dissolving the composition in a suitable liquid prior to the administering step.

Abbreviations used herein:
FVII Coagulation Factor VII in its single chain form
FVIIa Coagulation Factor VII in its cleaved, activated two-chain form
rFVII Recombinant Factor VII (recombinant Factor VIIa) (rFVIIa)

The following examples are offered by way of illustration, not by way of limitation:

EXAMPLES

Example 1

Compositions comprising Factor VII polypeptides and prepared according to Example 2 are shown. Typical excipients and their typical amounts are shown.

Table 1 shows the concentration of active ingredients and excipients in the event where the composition is in liquid form, that is, in the composition before finalising the manufacturing (e.g. finalising the freeze-drying), or in the reconstituted solution.

Table 2 shows the concentration of active ingredient and excipients in the event where the composition is in solid form, i.e. in freeze-dried form.

TABLE 1

Compositions, content of excipients in solution.

| Main Function: | Excipients: | Content (mg/ml) in liquid composition |
|---|---|---|
| Active Ingredient | rFVIIa | 0.6-5 |
| Tonicity modifier | Sodium Chloride | 0-4 |
| Tonicity modifier/ stabiliser | Calcium Chloride, $2H_2O$ | 1-7 |
| Buffering agent | Glycylglycine | 1.32 (0-1.5) |
| Surfactant | Polysorbate 80 | 0.05-2 |
| Bulking Agent/ Cryoprotectant/ Lyoprotectant | Mannitol | 10-40 |
| Bulking Agent/ Cryoprotectant/ Lyoprotectant | Sucrose | 10-40 |
| Antioxidant | Methionine | 0-1.0 |
|  | pH | 5-6 |

TABLE 2

Compositions, content of excipients in freeze-dried form.

| Main Function: | Excipients: | Content (% w/w) in solid composition |
|---|---|---|
| Active Ingredient | rFVIIa | 0.6-19 |
| Tonicity modifier | Sodium Chloride | 0-15 |
| Tonicity modifier/ stabiliser | Calcium Chloride, $2H_2O$ | 1.0 to 24.0 |
| Buffering agent | Glycylglycine | 0-6.0 |
| Surfactant | Polysorbate 80 | 0.05-8.0 |
| Bulking Agent/ Cryoprotectant/ Lyoprotectant | Mannitol | 13-76 |
| Bulking Agent/ Cryoprotetant/ Lyoprotectant | Sucrose | 13-76 |
| Antioxidant | Methionine | 0-4.2 |
|  | pH | 5-6 |

Example 2

Manufacturing of Compositions

In general, the compositions were prepared from a purified bulk solution. Excipients were added, and the solution was diluted to the desired concentration of rFVIIa. The resulting solution was sterile filtered using a sterilised membrane filter (0.2 micron pore size or equivalent) and filled into sterile glass vials. The vials were freeze-dried, stoppered and sealed with aluminium flip-off type caps.

Example 3

Compositions 1-19 comprising various amounts of sodium chloride, mannitol, sucrose and methionine and with various pH values were prepared according to the process described in Example 2. The compositions comprised fixed concentrations of Factor VII (1.0 mg/ml), Calcium Chloride, 2H₂0 (1.47 mg/ml), Glycylglycine (1.32 mg/ml) and Polysorbate 80 (1.0 mg/ml).

TABLE 3

Compositions 1-19.
Composition 1-19. Content of excipients mg/ml

| Composition No | NaCl | Mannitol | Sucrose | Methionine | pH |
|---|---|---|---|---|---|
| 1 | 0 | 10 | 10 | 0 | 6.0 |
| 2 | 3.5 | 10 | 10 | 0 | 5.0 |
| 3 | 0 | 40 | 10 | 0 | 5.0 |
| 4 | 3.5 | 40 | 10 | 0 | 6.0 |
| 5 | 0 | 10 | 40 | 0 | 5.0 |
| 6 | 3.5 | 10 | 40 | 0 | 6.0 |
| 7 | 0 | 40 | 40 | 0 | 6.0 |
| 8 | 3.5 | 40 | 40 | 0 | 5.0 |
| 9 | 0 | 10 | 10 | 0.5 | 5.0 |
| 10 | 3.5 | 10 | 10 | 0.5 | 6.0 |
| 11 | 0 | 40 | 10 | 0.5 | 6.0 |
| 12 | 3.5 | 40 | 10 | 0.5 | 5.0 |
| 13 | 0 | 10 | 40 | 0.5 | 6.0 |
| 14 | 3.5 | 10 | 40 | 0.5 | 5.0 |
| 15 | 0 | 40 | 40 | 0.5 | 5.0 |
| 16 | 3.5 | 40 | 40 | 0.5 | 6.0 |
| 17 | 1.75 | 25 | 25 | 0.25 | 5.5 |
| 18 | 1.75 | 25 | 25 | 0.25 | 5.5 |
| 19 | 1.75 | 25 | 25 | 0.25 | 5.5 |

Example 4

Analytical Methods used in Determining Stability Indicating Parameters

A. Determination of Oxidised Forms by Reverse Phase HPLC (RP-HPLC):

HPLC Column: 4.5×250 mm column packed with butyl-bonded silica with a particle size of 5 μm and pore size 300 Å. Column temperature: 70° C. Eluent A: water 99.9% v/v and trifluoracetic acid 0.1% v/v. Eluent B: acetonitrile 80% v/v. trifluoracetic acid 0.09% v/v and water 19.91% v/v. The column was eluted with a linear gradient from X% B to (X+13)% B in 30 minutes. Flow rate: 1.0 ml/min. Detection: 214 nm.

The oxidised forms are methionine sulfoxides of Factor VII Polypeptides. For example the two main derivatives of FVII are Met(O)298 FVII and Met(O)306 FVII.

The content of oxidised forms is expressed as the percentage of the initial amount of Factor VII in the composition upon preparation that is recovered as oxidised forms of Factor VII.

B. Determination of Aggregates of Factor VII Polypeptides by High Performance Gel Permeation Chromatography (GP-HPLC).

GP-HPLC was run on a Waters Protein Pak 300 SW column. 7.5×300 mm. using 0.2 M ammoniumsulfat pH 7.0 containing 5% isopropanol as the mobile phase. Flow rate: 0.5 ml/min and detection: 215 nm.

The content of aggregates is expressed as the percentage of the initial amount of Factor VII in the composition upon preparation that is recovered as dimeric, oligomeric and polymeric forms of Factor VII.

Example 5

Content of Oxidised Forms of Factor VIIa after Termination of the Freeze-Drying Process and Upon Storage Compositions 1-19 of Example 3 were analysed by method A (Example 4) for content of oxidised forms upon termination of the freeze-drying and upon 2 and 8 months of storage at 30° C.

TABLE 4

Content of oxidised forms and increase thereof upon storage for 8 months.
% of the initial content of Factor VIIa recovered as oxidised forms.

| Composition No | 0 | 2 | 8 | increase 0-8 months |
|---|---|---|---|---|
| 1 | 2.5 | 3.5 | 4.8 | 2.3 |
| 2 | 2.7 | 3 | 6.1 | 3.4 |
| 3 | 2.3 | 3.7 | 7 | 4.7 |
| 4 | 2.7 | 5.5 | 12 | 9.3 |
| 5 | 2.6 | 3.6 | 5.3 | 2.7 |
| 6 | 2.7 | 3.3 | 5.8 | 3.1 |
| 7 | 3 | 3.5 | 5.2 | 2.2 |
| 8 | 2.3 | 2.9 | 3.4 | 1.1 |
| 9 | 1.6 | 1.5 | 1.7 | 0.1 |
| 10 | 1.7 | 1.7 | 2.1 | 0.4 |
| 11 | 1.7 | 1.8 | 2.5 | 0.8 |
| 12 | 1.6 | 1.6 | 1.9 | 0.3 |
| 13 | 1.7 | 1.6 | 1.7 | 0 |
| 14 | 1.6 | 1.5 | 1.6 | 0 |
| 15 | 1.6 | 1.5 | 1.8 | 0.2 |
| 16 | 1.7 | 1.6 | 1.8 | 0.1 |
| 17 | 1.7 | 1.6 | n.a. | n.a. |
| 18 | 1.7 | 1.6 | 1.9 | 0.2 |
| 19 | 1.7 | 1.6 | 1.8 | 0.1 | n.a. not analysed

A statistical analysis shows that compositions comprising methionine are more stable towards oxidative degradation.

Example 6

Content of Aggregates of Factor VIIa after Termination of the Freeze-Drying Process and Upon Storage Compositions 1-19 of Example 3 were analysed by method B (Example 4) for content of aggregates upon termination of the freeze-drying and upon 2 and 8 months of storage at 30° C.

TABLE 5

Content of aggregates and their increase upon storage for 8 months.
% of the initial content of Factor VIIa recovered as aggregates.

| Composition No | 0 | 2 | 8 | increase 0-8 months |
|---|---|---|---|---|
| 1 | 0.7 | 0.8 | 0.9 | 0.2 |
| 2 | 1 | 2 | 2.9 | 1.9 |
| 3 | 1.5 | 2.5 | 3.5 | 2 |
| 4 | 1.1 | 2.1 | 3.1 | 2 |
| 5 | 0.8 | 1 | 1.1 | 0.3 |
| 6 | 0.8 | 1.2 | 1.1 | 0.3 |
| 7 | 0.9 | 1 | 0.9 | 0 |
| 8 | 0.9 | 1 | 1.2 | 0.3 |
| 9 | 0.9 | 1 | 1.1 | 0.2 |
| 10 | 0.8 | 1.7 | 2.5 | 1.7 |
| 11 | 1 | 1.2 | 1.5 | 0.5 |
| 12 | 1.3 | 2 | 2.8 | 1.5 |
| 13 | 0.7 | 0.8 | 0.9 | 0.2 |

TABLE 5-continued

Content of aggregates and their increase upon storage for 8 months.
% of the initial content of Factor VIIa recovered as aggregates.

| Composition No | 0 | 2 | 8 | increase 0-8 months |
|---|---|---|---|---|
| 14 | 1 | 1.7 | 1.4 | 0.4 |
| 15 | 1.1 | 1.4 | 1.5 | 0.4 |
| 16 | 0.8 | 0.9 | 1 | 0.2 |
| 17 | 0.9 | 1.1 | n.a. | n.a. |
| 18 | 0.8 | 1 | 1.5 | 0.7 |
| 19 | 1 | 1 | 1.1 | 0.1 | n.a. not analysed

A statistical analysis shows that the presence of sucrose in the compositions is important in order to decrease formation of aggregates.

Example 7

Content of Dimeric and Oligomeric Forms of Factor VIIa after Termination of the Freeze-Drying Process Composition A comprising polyol and saccharide as listed in the table below was prepared according to the process described in Example 2. The composition further comprised Factor VIIa (1.0 mg/ml), calcium chloride 2 H2O (1.47 mg/ml), glycylglycine (1.32 mg/ml) and polysorbate 80 (0.7 mg/ml). pH was 5.0.

Composition A was analysed by method B (Example 4) for content of aggregates upon termination of the freeze-drying and upon 1 and 2 months of storage at 30° C. The table lists the % of the initial content of Factor VIIa recovered as aggregates:

TABLE 6

% of the initial content of Factor VIIa recovered as aggregates.

| | | Months | | |
|---|---|---|---|---|
| Composition | Additives | 0 | 1 | 2 |
| A | Mannitol 25 mg/ml Trehalose 15 mg/ml | 1.1 | 2.0 | 1.7 |

Example 8

Structural stability of the freeze-dried cake is shown for various compositions, 1-19, see Example 3. The ratio of mannitol to sucrose is reported of each composition.

TABLE 7

Stability of the freeze-dried cake according to the ratio between mannitol and sucrose

| | Compositions | | | |
|---|---|---|---|---|
| | 5, 6, 13, 14 | 1, 2, 7, 8, 9, 10, 15, 16 | 17, 18 and 19 | 3, 4, 11, 12 |
| Weight Ratio of Man:Suc | 1:4 | 1:1 | 1:1 | 4:1 |
| Freeze-dried cake | C | OK | OK | OK |

C: collapsed cake,
Man: Mannitol,
Suc: Sucrose,
OK: slightly collapsed or not collapsed Example 9

The following formulations were prepared as described in example 2 using filling volumes of 1 and 5 ml:

| | Formulation | | |
|---|---|---|---|
| | A | B | C |
| rFVIIa (mg/ml) | 0.6 | 1.0 | 1.0 |
| CaCl$_2$ (mM) | 10 | 10 | 10 |
| Glycylglycine | 10 | 10 | 10 |
| L-Histidine (mM) | — | 10 | 10 |
| NaCl (mM) | 50 | 39 | 39 |
| Tween 80 (mg/ml) | 0.038 | 0.07 | 0.07 |
| Methionine (mg/ml) | — | 0.5 | 2.0 |
| Mannitol (mg/ml) | 30 | 25 | 25 |
| Sucrose (mg/ml) | — | 10 | 10 |
| Ph | 5.5 | 5.5 | 5.5 |

The stability of the formulations was investigated at 25° C., 30° C., and 40° C. and the following results were obtained. The vials were reconstituted in water before analysis.
Dimer and Oligomer Forms
The contents of dimer and oligomer forms were measured by GP-HPLC as described in example 4. All results are stated in %.
5 ml filling volume:

| | | ½ | 3 months | | | 6 |
|---|---|---|---|---|---|---|
| Formulation | 0 months | month 40° C. | 1 month 40° C. | 40° C. | 30° C. | 25° C. | months 25° C. |
| A | 3.3 | 5.5 | 6.4 | 8.0 | 6.0 | 6.3 | 6.3 |
| B | 2.3 | 2.7 | 2.8 | 3.0 | 2.7 | 3.2 | 3.0 |
| C | 4.0 | 4.2 | 4.6 | 4.7 | 4.3 | 4.4 | 4.4 |

1 ml filling volume:

| | | 3 months | | |
|---|---|---|---|---|
| Formulation | 0 months | 40° C. | 30° C. | 25° C. |
| A | 2.7 | 11.0 | 7.0 | 6.5 |
| B | 2.2 | 7.4 | 3.4 | 2.9 |
| C | 3.3 | 6.9 | 3.8 | 3.7 |

Figure 2A:
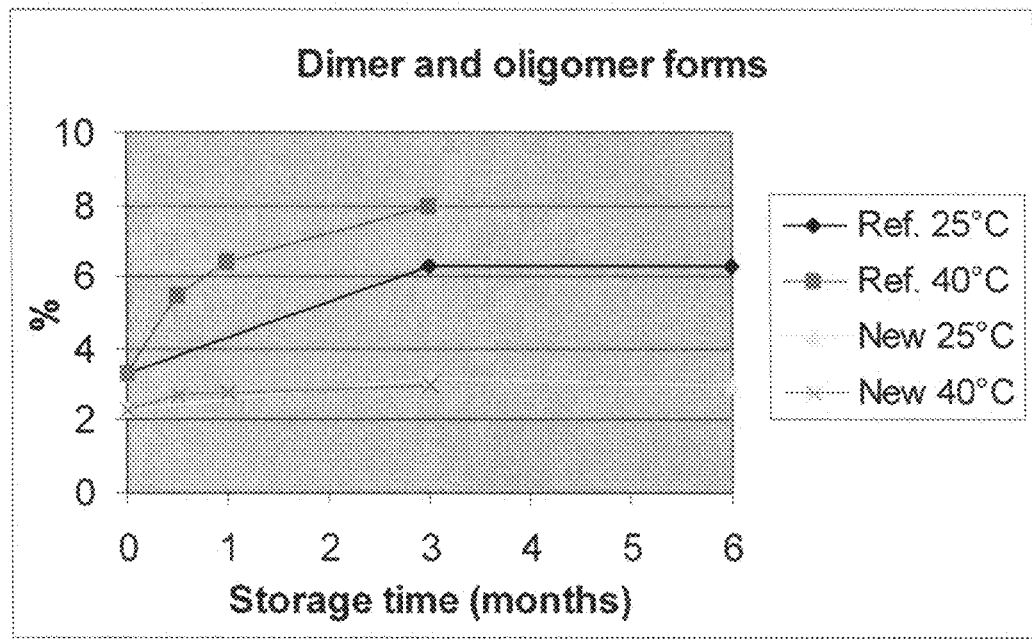
FIGS. 2A and 2B show the contents of aggregate forms for dimmer, oligomer, and oxidized forms of the formulations of the invention.

Furthermore, the contents of aggregate forms for formulation A (=Ref) and formulation B (=New), filling volume 5 ml, can be seen from FIG. 2a.
Oxidised Forms
The contents of oxidised forms were measured by RP-HPLC as described in example 4.
5 ml filling volume:

| | | ½ | 3 months | | | 6 |
|---|---|---|---|---|---|---|
| Formulation | 0 months | month 40° C. | 1 month 40° C. | 40° C. | 30° C. | 25° C. | months 25° C. |
| A | 2.1 | 2.8 | 3.4 | 4.0 | 3.4 | 3.1 | 3.5 |
| B | 1.3 | 1.3 | 1.6 | 1.3 | 1.6 | 1.6 | 1.4 |
| C | 1.2 | 1.4 | 1.6 | 1.8 | 1.6 | 1.6 | 1.3 |

1 ml filling volume:

| Formulation | 0 months | 3 months | | |
|---|---|---|---|---|
| | | 40° C. | 30° C. | 25° C. |
| A | 2.5 | 4.6 | 4.0 | 5.3 |
| B | 1.3 | 2.0 | 1.1 | 1.8 |
| C | 1.3 | 1.8 | 1.7 | 1.5 |

Figure 2B:
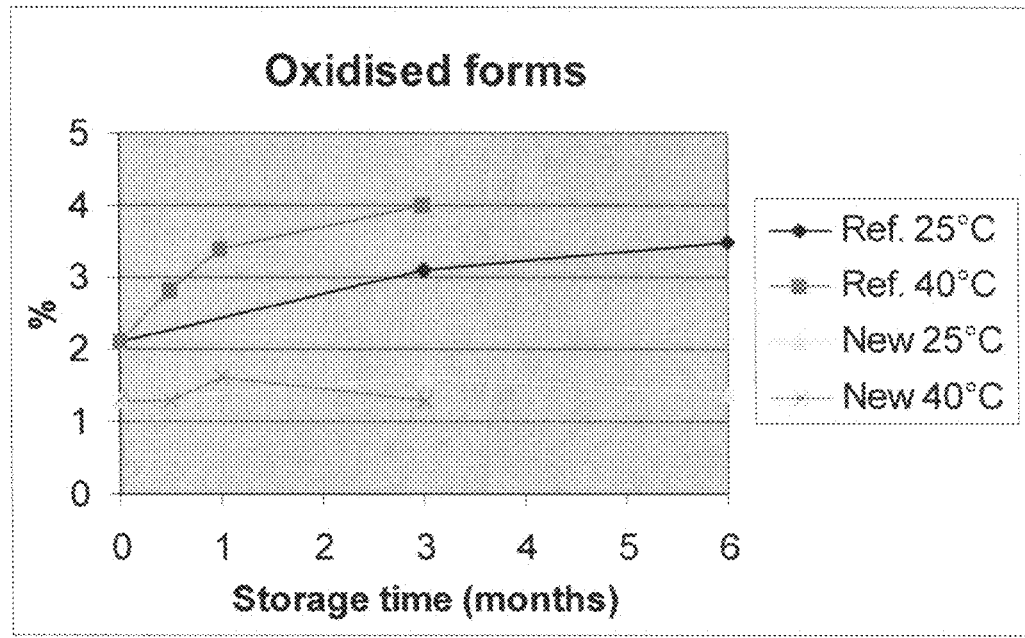

Furthermore, the contents of oxidized forms for formulation A (=Ref) and formulation B (=New), filling volume 5 ml, can be seen from FIG. 2b.

Activity

The activity was measured by one stage clotting assay as described in example 12 for formulations, which had been stored at 30° C. for 3 months. The specific activity was calculated based on the content of rFVIIa in the formulations and the following results were obtained:

| Formulation | Specific activity (IU/mg) |
|---|---|
| A | 50523 |
| B | 58373 |
| C | 60318 |

Interpretation of Results:

The results show, that formulations B and C, which contain mannitol, sucrose, and methionine are more stable—i.e. shows a slower increase in contents of dimer and oligomer forms and oxidised forms. In accordance, the activities of these formulations are higher as measured after 3 months' storage at 30° C.

Example 10

The following formulations were prepared as described in example 2 using a filling volume of 5 ml.

| | Formulation | | | | |
|---|---|---|---|---|---|
| | A | B | C | D | E |
| rFVIIa (mg/ml) | 1.0 | 1.0 | 1.0 | 1.0 | 1.0 |
| CaCl$_2$ (mM) | 10 | 10 | 10 | 10 | 10 |
| Glycylglycine (mM) | 10 | 10 | 10 | 10 | 10 |
| L-Histidine (mM) | 10 | 10 | 10 | 10 | 10 |
| NaCl (mM) | 39 | 39 | 39 | 39 | 39 |
| Methionine (mg/ml) | 0.5 | 0.5 | 0.5 | 0.5 | 0.5 |
| Tween 20 (mg/ml) | 0.1 | | | | |
| Tween 80 (mg/ml) | | 0.1 | | | |
| Poloxamer 188 (mg/ml) | | | 1.0 | | |
| Brij 35 (mg/ml) | | | | 0.1 | |
| Mannitol (mg/ml) | 25 | 25 | 25 | 25 | 25 |
| Sucrose (mg/ml) | 10 | 10 | 10 | 10 | 10 |
| pH | 5.5 | 5.5 | 5.5 | 5.5 | 5.5 |

The vials were reconstituted in water and subjected to shaking for 19 hours in order to test the physical stability of the formulations. The effect of shaking was investigated by visual inspection and measurement of the UV absorbance at 400 nm (=Abs in the table below). The results below clearly show the increased physical stability obtained by addition of a detergent.

| | Before shaking | | After shaking | |
|---|---|---|---|---|
| Formulation | Visual appearance | Abs | Visual appearance | Abs |
| A | Clear liquid | 0.01 | Clear liquid with few particles | 0.01 |
| B | Clear liquid | 0.00 | Slightly turbid | 0.36 |
| C | Clear liquid | 0.00 | Clear liquid with few particles | 0.00 |
| D | Clear liquid | 0.00 | Clear liquid with few particles | 0.00 |
| E | Clear liquid | 0.01 | Turbid | 2.18 |

Example 11

Six formulation were prepared as described in example 2. The composition of the formulations was:

| | |
|---|---|
| rFVIIa | 1.0 mg/ml |
| CaCl$_2$ | 10 mM |
| Glycylglycine | 10 mM |
| L-Histidin | 10 mM |
| NaCl | 39 mM |
| Tween 80 | 0.07 mg/ml |
| Mannitol | 25 mg/ml |
| Sucrose | 10 mg/ml |

Each of the six formulations were adjusted to a different pH:

Formulation A: pH 5.0

Formulation B: pH 5.5

Formulation C: pH 6.0

Formulation D: pH 6.5

Formulation E: pH 7.0

Formulation F: pH 7.5

Figure 1B:
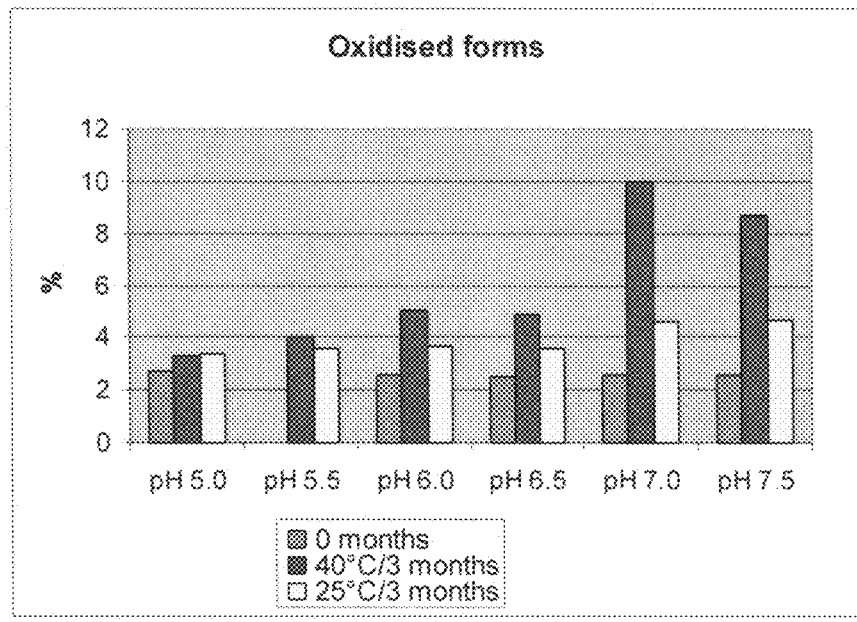

The stability of the six formulations was investigated for vials stored at 25° C. and 40° C. The results shown in the Tables below (and FIGS. 1a and 1b) were obtained.

| | Dimer and oligomer forms (aggregates) (%) | | |
|---|---|---|---|
| Formulation | 0 MONTHS | 40° C./3 MONTHS | 25° C./3 MONTHS |
| A | 2.2 | 3.8 | 2.5 |
| B | 1.7 | 3.2 | 1.9 |
| C | 1.5 | 2.7 | 1.7 |
| D | 1.1 | 1.9 | 1.3 |
| E | 0.8 | 1.6 | 1.0 |
| F | 0.8 | 1.6 | 1.0 |

| | Oxidised forms (%) | | |
|---|---|---|---|
| Formulation | 0 MONTHS | 40° C./3 MONTHS | 25° C./3 MONTHS |
| A | 2.7 | 3.3 | 3.4 |
| B | N/A | 4.0 | 3.6 |
| C | 2.6 | 5.0 | 3.7 |
| D | 2.5 | 4.9 | 3.6 |
| E | 2.6 | 10.0 | 4.6 |
| F | 2.6 | 8.7 | 4.7 |

The contents of dimers and oligomer forms and oxidised forms were determined as described in example 4.

Example 12

Assays for Testing Biological Activity of Factor VII Polypeptides

Test for Factor VIIa Activity:

A suitable assay for testing for Factor VIIa activity and thereby selecting suitable Factor VIIa variants can be performed as a simple preliminary in vitro test: (the "In Vitro Hydrolysis Assay").

In Vitro Hydrolysis Assay

Native (wild-type) Factor VIIa and Factor VIIa variant (both hereafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a Spectra Max™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

$$\text{Ratio} = (A_{405\,nm}\text{ Factor VIIa variant})/(A_{405\,nm}\text{ Factor VIIa wild-type}).$$

Based thereon, Factor VIIa variants with an activity comparable to or higher than native Factor VIIa may be identified, such as, for example, variants where the ratio between the activity of the variant and the activity of native Factor VII (wild-type FVII) is around, versus above 1.0.

The activity of Factor VIIa or Factor VIIa variants may also be measured using a physiological substrate such as Factor X, suitably at a concentration of 100-1000 nM, where the Factor Xa generated is measured after the addition of a suitable chromogenic substrate (eg. S-2765) ("the In Vitro Proteolysis Assay"). In addition, the activity assay may be run at physiological temperature.

In Vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl2 and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a Spectra-Max™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

$$\text{Ratio} = (A405\text{ nm Factor VIIa variant})/(A405\text{ nm Factor VIIa wild-type}).$$

Based thereon, Factor VIIa variants with an activity comparable to or higher than native Factor VIIa may be identified, such as, for example, variants where the ratio between the activity of the variant and the activity of native Factor VII (wild-type FVII) is around, versus above 1.0.

Thrombin Generation Assay:

The ability of Factor VII or Factor VII-related polypeptides or Factor VIII or Factor VIII-related polypeptides (e.g., variants) to generate thrombin can be measured in an assay comprising all relevant coagulation Factors and inhibitors at physiological concentrations and activated platelets (as described on p. 543 in Monroe et al. (1997) Brit. J. Haematol. 99, 542-547 which is hereby incorporated as reference).

Clot Assay:

The activity of the Factor VII polypeptides may also be measured using a one-stage clot assay (assay 4) essentially as described in WO 92/15686 or U.S. Pat. No. 5,997,864. Briefly, the sample to be tested is diluted in 50 mM Tris (pH 7.5), 0.1% BSA and 100 μL is incubated with 100 μL of Factor VII deficient plasma and 200 μL of thromboplastin C containing 10 mM $Ca^{2+}$. Clotting times are measured and compared to a standard curve using a reference standard or a pool of citrated normal human plasma in serial dilution.

The invention claimed is:

1. A composition comprising a Factor VII polypeptide; about 0.1 to 5 mg/ml of an antioxidant; about 5 to 20 mg/ml of a saccharide; and about 10 to 40 mg/ml of a polyol, said composition having a moisture content of not more than about 3%, wherein said Factor VII polypeptide is wild type human Factor VII or a polypeptide exhibiting substantially the same or improved biological activity relative to wild type human Factor VII.

2. The composition according to claim 1, wherein the antioxidant is selected from the group consisting of homocysteine, cysteine, cystathionine, methionine, gluthatione, and peptides containing any one of homocysteine, cysteine, cystathionine, methionine, and gluthatione.

3. The composition according to claim 1, wherein the saccharide is selected from the group consisting of sucrose, dextrose, lactose, maltose, trehalose, cyclodextrins, maltodextrins and dextrans.

4. The composition according to claim 1, wherein the polyol is selected from the group consisting of mannitol, sorbitol and xylitol.

5. The composition according to claim 1, wherein the composition is stable such that not more than about 5% w/w of the initial content of Factor VII polypeptide is converted to aggregates upon storage of said composition at 30° C. for 8 months.

6. The composition according to claim 1, wherein the composition is stable such that not more than about 6% w/w of the initial content of Factor VII polypeptide is converted to oxidised forms upon storage of said composition at 30° C. for 8 months.

7. The composition according to claim 1, further comprising an agent suitable for keeping the pH of said composition in the range of 3 to 9 when dissolved in aqueous solvent.

8. The composition according to claim 7, wherein said agent is selected from the group consisting of citrate, acetate, histidine, malate, phosphate, tartaric acid, succinic acid, MES, HEPES, PIPES, imidazol, TRIS, lactate, glutamate and glycylglycine.

9. The composition according to claim 1, further comprising a tonicity modifier.

10. The composition according to claim 9, wherein the tonicity modifier is selected from the group consisting of sodium acetate, sodium lactate, sodium chloride, potassium chloride and calcium chloride.

11. The composition according to claim 1, further comprising a surfactant.

12. The composition according to claim 11, wherein the surfactant is selected from the group consisting of polysorbates; polyoxyethylene alkyl ethers; poloxamers; ethylene/polypropylene block polymers; and polyethyleneglycols (PEGs).

13. The composition according to claim 1, further comprising one or more other pharmaceutical excipients acting as a bulking agent.

14. The composition according to claim 1, wherein the saccharide is sucrose.

15. The composition according to claim 1, wherein the polyol is mannitol.

16. The composition according to claim 1, wherein the Factor VII Polypeptide is selected from the group consisting of Human Factor VIIa and a Factor VII Sequence Variant.

17. The composition according to claim 16, wherein the Factor VII Polypeptide is recombinant human Factor VIIa.

18. The composition according to claim 1, wherein the Factor VII Polypeptide is a Factor VII-related polypeptide and wherein the ratio between the activity of said Factor VII-related polypeptide and wild-type Factor VII is at least 1.25 when tested in an in vitro proteolysis assay or in an in vitro hydrolysis assay.

19. The composition according claim 16, wherein Factor VII polypeptide is present in a concentration of from about 0.6 mg/ml to about 10.0 mg/ml.

20. The composition according to claim 1, wherein said moisture content is not more than about 2.5% w/w.

21. The composition according to claim 1, wherein the composition is a lyophilised cake.

22. The composition according to claim 11, wherein the surfactant is selected from the group consisting of a polysorbate and a poloxamer.

23. The composition according to claim 1, wherein the antioxidant is methionine.

24. The composition according to claim 1, further comprising L-histidine.

25. The composition according to claim 1, further comprising one or more components selected from the group consisting of: $CaCl_2$, NaCl, and Glycylglycine.

26. A composition according to claim 1 wherein
Factor VII is 1 mg/ml;
mannitol is 25 mg/ml;
sucrose is 10 mg/ml;
and methionine is 0.5 mg/ml.

27. A composition according to claim 26,
further comprising 10 mM CaCl2.

28. The composition according to claim 26, wherein
Factor VII is 1 mg/ml;
mannitol is 25 mg/ml;
sucrose is 10 mg/ml; and
methionine is 0.5 mg/ml.

* * * * *

UNITED STATES PATENT AND TRADEMARK OFFICE
CERTIFICATE OF CORRECTION

| | | |
|---|---|---|
| PATENT NO. | : 8,729,022 B2 | Page 1 of 1 |
| APPLICATION NO. | : 13/573310 | |
| DATED | : May 20, 2014 | |
| INVENTOR(S) | : Jensen et al. | |

It is certified that error appears in the above-identified patent and that said Letters Patent is hereby corrected as shown below:

In the Claims:

Column 32, claim 26, line 15-19, should read as follows:

~~A~~ The composition according to claim 1, wherein the polyol is mannitol, the saccharide is sucrose, and the antioxidant is methionine ~~wherein~~
~~Factor VII is 1mg/ml;~~
~~mannitol is 25 mg/ml;~~
~~sucrose is 10 mg/ml;~~
~~and methionine is 0.5 mg/ ml.~~

Column 32, claim 27, line 20-21, should read as follows:

~~A~~ The composition according to claim 28 ~~26~~, further comprising 10mM CaCl$_2$.

Signed and Sealed this
Twenty-third Day of September, 2014

Michelle K. Lee
*Deputy Director of the United States Patent and Trademark Office*